US012811017B2

(12) United States Patent
Bauder et al.

(10) Patent No.: US 12,811,017 B2
(45) Date of Patent: Nov. 24, 2026

(54) NEAR REAL TIME HEALTH DATA COMMUNICATION TO PUBLIC SAFETY ANSWERING POINT AND/OR ONE OR MORE FIRST RESPONDERS

(71) Applicant: Intrado Life & Safety, Inc., Longmont, CO (US)

(72) Inventors: Matthew Ross Bauder, Berthoud, CO (US); Luke James Rutherford, Longmont, CO (US)

(73) Assignee: Intrado Life & Safety, Inc., Longmont, CO (US)

( * ) Notice: Subject to any disclaimer, the term of this patent is extended or adjusted under 35 U.S.C. 154(b) by 0 days.

(21) Appl. No.: 18/781,366

(22) Filed: Jul. 23, 2024

(65) Prior Publication Data

US 2026/0031244 A1 Jan. 29, 2026

(51) Int. Cl.
*G16H 80/00* (2018.01)
*H04W 12/08* (2021.01)

(52) U.S. Cl.
CPC ............ *G16H 80/00* (2018.01); *H04W 12/08* (2013.01)

(58) Field of Classification Search
CPC ....... G16H 80/00; H04W 40/12; H04W 12/08
USPC .............................................................. 705/2
See application file for complete search history.

(56) References Cited

U.S. PATENT DOCUMENTS 6,154,658 A 11/2000 Caci
2009/0186596 A1* 7/2009 Kaltsukis ............... H04M 11/04 455/404.2
2010/0317317 A1* 12/2010 Maier ................... H04W 4/029 455/404.2
2013/0194092 A1 8/2013 Moriarty et al.
2017/0215056 A1 7/2017 Edge et al.
2019/0174289 A1 6/2019 Martin et al.
2020/0135005 A1 4/2020 Katz et al.
2021/0249144 A1* 8/2021 Chiu ...................... G16H 40/20
2022/0279331 A1 9/2022 Biegel et al.
2023/0007483 A1* 1/2023 Mueck ................ H04W 12/069

OTHER PUBLICATIONS

USPTO, Non-Final Office Action in U.S. Appl. No. 18/781,411 dated Jan. 7, 2026, 11 pages.
USPTO, Non-Final Office Action in U.S. Appl. No. 18/781,411 dated Jun. 29, 2026, 10 pages.
USPTO, Final Rejection in U.S. Appl. No. 18/781,411 dated Apr. 24, 2026, 11 pages.
USPTO, Notice of Allowance in U.S. Appl. No. 18/781,411 dated Aug. 7, 2026, 9 pages.

* cited by examiner

*Primary Examiner* — Hiep V Nguyen
(74) *Attorney, Agent, or Firm* — Patent Capital Group

(57) ABSTRACT

Particular example embodiments described herein can provide for a system, an apparatus, and a method for enabling near real time communication of health data to a public safety answering point (PSAP) and/or first responders. In an example the system includes receiving, at a public safety answering point (PSAP), from a device, an emergency communication related to a user, receiving, from the device, an authorization to access near real time health data for the user stored in a secure location, using the authorization to access the near real time health data related to the user, and receiving from the secure location, the near real time health data related to the user. In some examples, the near real time health data is communicated to a first responder responding to the emergency communication.

20 Claims, 17 Drawing Sheets

NEAR REAL TIME HEALTH DATA COMMUNICATION TO PUBLIC SAFETY ANSWERING POINT AND/OR ONE OR MORE FIRST RESPONDERS

TECHNICAL FIELD

This disclosure relates in general to the field of computing and/or networking and, more particularly, to a system, an apparatus, and a method to enable near real time communication of health data to a public safety answering point (PSAP) and/or one or more first responders.

BACKGROUND

A public safety answering point (PSAP), sometimes called a public safety access point, is a call center where emergency/non-emergency calls (like police, fire brigade, ambulance) are received and handled. The PSAP is a call center in almost all countries, including Canada and the United States, where a trained PSAP operator is typically responsible for answering calls to an emergency telephone number for police, firefighting, and ambulance services.

In Canada and the United States, counties are generally bound to provide a PSAP and other emergency services even within municipalities, unless the municipality chooses to opt out and have its own system. Each PSAP has a 'real' telephone number that is called when an emergency number (e.g., 911) is dialed or texted. The telecommunications operator is responsible for associating all landline numbers with the most applicable (often the nearest) PSAP, such that when the emergency number is dialed, the call or text is automatically routed to the most suitable PSAP.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

Figure 1A:
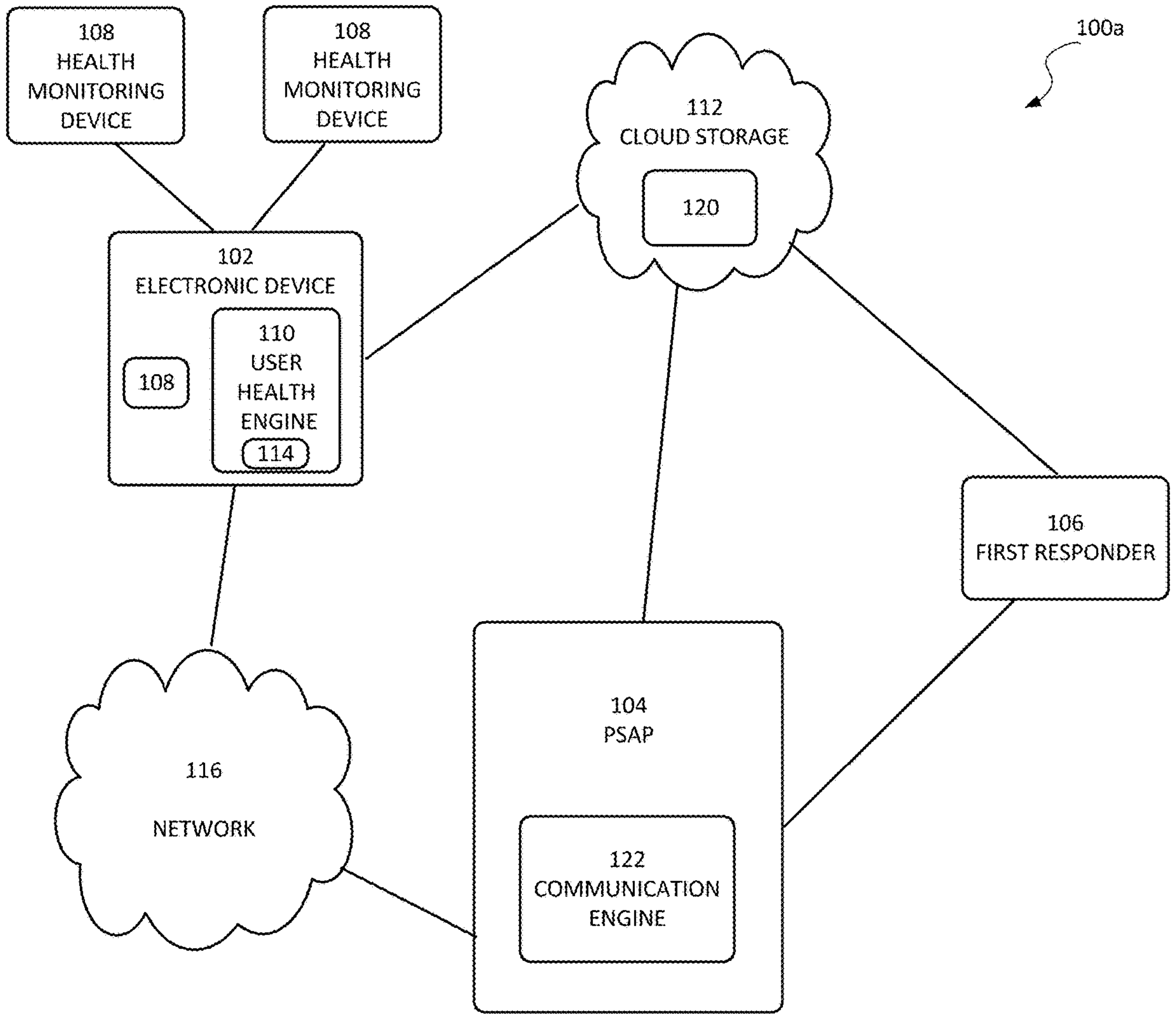
FIG. 1A is a simplified block diagram of a system to enable near real time health data communication to a public safety answering point (PSAP) and/or first responders, in accordance with an embodiment of the present disclosure.

The FIGURES of the drawings are not necessarily drawn to scale, as their dimensions can be varied without departing from the scope of the present disclosure.

DETAILED DESCRIPTION

The following detailed description sets forth examples of apparatuses, methods, and systems relating to enabling near real time communication of health data to a PSAP and/or one or more first responders, in accordance with an embodiment of the present disclosure. Features such as structure(s), function(s), and/or characteristic(s), for example, are described with reference to one embodiment as a matter of convenience; various embodiments may be implemented with any suitable one or more of the described features.

Overview

Smart health monitoring devices are devices that can monitor one or more health indicators of a user and include biosensors, fitness trackers, smart health monitoring watches, smart health monitoring bracelets, smart health monitoring glasses, smart health monitoring socks, smart health monitoring shoe inserts, smart health monitoring clothing, smart health monitoring necklaces, smart health monitoring rings, smart health monitoring earrings, smart health monitoring headbands, smart health monitoring belts, smart health monitoring patches, smart health monitoring sleep tracking mats, smart health monitoring helmets, smart health monitoring headwear, electrocardiogram (ECG) monitors, blood pressure monitors, otoscopes, portable diagnostic devices, pulse oximeter, and other health monitoring devices that can monitor one or more health indicators of a user. These systems make the detecting, monitoring, and recording of bio-signals of a user portable and have the ability to track health indicators like heart rate, temperature, oxygen saturation ($Sp0_2$), blood pressure, blood glucose levels, stress levels, ECG, and other health indicators. With smart health monitoring devices, users have the ability to collect their own near real time health data and store the near real time health data in a secure location to protect the privacy of the user. During a medical emergency, it would be beneficial if a public safety answering point (PSAP) and/or first responders had access to the near real time health data of a user to allow the PSAP and/or the first responders to have some insights into the current condition of the person with the medical emergency.

In an example, a system, method, apparatus, means, etc. can help to enable communication to first responders of near real time health data of a user collected by one or more smart health monitoring devices. The term "near real time health data of a user" and "real time health data" includes a biometric reading of a condition of the user that is less than five (5) minutes old (e.g., less than four (4) minutes old, less than three (3) minutes old, less than two (2) minutes old, less than 1.5 minutes old, less than one (1) minute old, less than thirty (30) seconds old, one second old, etc.). For example, near real time health data is health data that includes a biometric reading of a condition of the user that has been collected within less than five (5) minutes from when the health data is received by the first responder. When the PSAP and/or the first responder receive the health data for the user, the health data includes a biometric reading of a condition of the user that allows the PSAP and/or the first responder to gain an insight into the current health condition of the user.

For example, one or more health monitoring devices can collect health data for a user and the health data can be stored in a secure location (e.g., cloud storage, secured memory, or some other secure location). When the user sends a communication (e.g., a voice call, text (e.g. SMS message), video call, or some other communication) to a PSAP about a medical emergency the user is experiencing, the PSAP sends a request for authorization to access the health data stored in the secure location. The PSAP can receive a key, certificate, password, token, or some other type of authorization that will allow the PSAP to access the health data in the secure location. The health data and any updated health data that has been communicated to the secure location from the one or more smart health monitoring devices is communication to first responders responding to the medical emergency the user is experiencing to allow the first responders to obtain details of the medical emergency experienced by the user and to help the first responders be better prepared to respond to the medical emergency when the first responders arrive to help the user. In some examples, the PSAP receives the authorization, receives the health data and any updated health data, and communicates the authorization to the first responders to enable the first responders to access the health data and any updated health data. In some examples, the PSAP receives the authorization, does not receive or access the health data and any updated health data, and communicates the authorization to the first responders to enable the first responders to access the health data and any updated health data.

In some examples, the communication along with the authorization to access the health data stored in the secure location is automatically sent to the PSAP. More specifically, if the user is unconscious, is suffering from dangerously low blood sugar, is having a heart attack, or is otherwise incapacitated or potentially suffering a life-threatening medical emergency, the communication and the authorization to access the health data stored in the secure location can be automatically sent to the PSAP regarding the medical emergency. In some examples, the user can pre-program or pre-provision an electronic device to send the health data authorization with the communication to the PSAP so the authorization is automatically communicated along with any communication to the PSAP. In some examples, automatically sending the authorization with the communication to the PSAP can be pre-programmed or pre-provisioned by the user (e.g., an opt out or opt in setting). The term "automatically" includes without a direct user action. For example, a user can pre-program or pre-provision the electronic device to send a communication and/or authorization without any user action when a specific event or condition occurs. Then, when the specific event or condition occurs, the communication and/or authorization is sent without a direct user action.

Example Systems, Apparatuses, and Methods

FIG. 1A is simplified block diagram of a particular non-limiting health data communication system 100*a* to enable near real time health data communication to a PSAP and/or one or more first responders, in accordance with an embodiment of the present disclosure. As illustrated in FIG. 1A, the health data communication system 100*a* can include an electronic device 102, a public safety answering point (PSAP) 104, and first responder device 106. The electronic device 102 can be a phone, smart phone, tablet, laptop computer, computer, or any other electronic device that a user may use to communicate with the PSAP 104 and can access near real time health data for the user. The first responder device 106 is an electronic device used by one or more first responders to access the near real time health data. The one or more first responders are individuals designated or trained to respond to an emergency and can be an emergency response team. The PSAP 104 can include a communication engine 122. The communication engine 122 helps to facilitate communications to and from the PSAP 104, can help facilitate requests to access near real time health data of a user, can communicate the near real time health data of the user to the first responder device 106, and, in some examples, can communicate the authorization to access the near real time health data of the user to the first responder device 106. The near real time health data includes a biometric reading of a condition of the user that is less than five (5) minutes old (e.g., less than five (5) minutes from when the health data was collected to when it was available to the first responder device 106 and/or the first responder). For example, the near real time health data includes a biometric reading of a condition of the user can be less than four (4) minutes old, less than three (3) minutes old, less than two (2) minutes old, less than 1.5 minutes old, less than one (1) minute old, less than thirty (30) seconds old, less than fifteen (15) seconds old, less than one (1) second old, or some other time period that is less than five (5) minutes from when the health data was collected to when it was available to the first responder device 106 and/or the first responder.

In an example, one or more health monitoring devices 108 are in communication with the electronic device 102. In some examples, the electronic device includes a health monitoring device 108. Each health monitoring device 108 can monitor health data of the user including heart rate, temperature, oxygen saturation ($Sp0_2$), blood pressure, glucose, ECG, and/or other health indicators of the user. The electronic device 102 can include a user health engine 110 that can collect near real time health data 120 and store the near real time health data 120 in cloud storage 112. In some examples, the user health engine 110 can include health data authorization 114 that allows the user health engine 110 and the electronic device 102 to access the near real time health data 120 stored in the cloud storage 112. In some examples, the health data authorization 114 can be stored in the electronic device 102.

In an illustrative example, a user of the electronic device 102 may experience a medical emergency (e.g., heart attack, fall, injury, etc.) and the user may send a communication to the PSAP 104 about the medical emergency using network 116. The communication to the PSAP 104 can be a voice call, text (e.g. SMS message), video call, or some other communication to the PSAP 104 about the medical emergency. In some examples, the communication to the PSAP 104 is automatically sent in response to a detected possible medical emergency (e.g., a detected fall by the user, a detected dangerously low heart rate of the user, a detected dangerously low blood sugar level of the user, etc.). The PSAP 104 can obtain the health data authorization 114, access the near real time health data 120 stored in the cloud storage 112, and communicate the near real time health data 120 to the first responder device 106. By providing the first responder device 106 with the near real time health data 120, the first responder can access the real time health data 120 and gain insight into the medical emergency experienced by the user and may be better prepared to respond to the medical emergency when the first responder arrives to help the user.

In some examples, the PSAP does not obtain or access the near real time health data 120 of the user and communicates the health data authorization 114 to the first responder device 106. The first responder device 106 uses the health data authorization 114 to access the near real time health data 120 for the user in the cloud storage 112. In some examples the authorization can be automatically sent to the PSAP 104. For example, the user can pre-program or pre-provision the electronic device 102 to automatically send the health data authorization 114 along with the communication to the PSAP 104. In some examples, if the user is incapacitated, is in a vehicle accident, having a life-threatening medical emergency (e.g., if the heart rate is below a certain beat per minute), or some other threshold that may be triggered, the electronic device 102 may automatically send the health data authorization 114 to the PSAP 104 along with the communication to the PSAP 104.

Figure 1B:
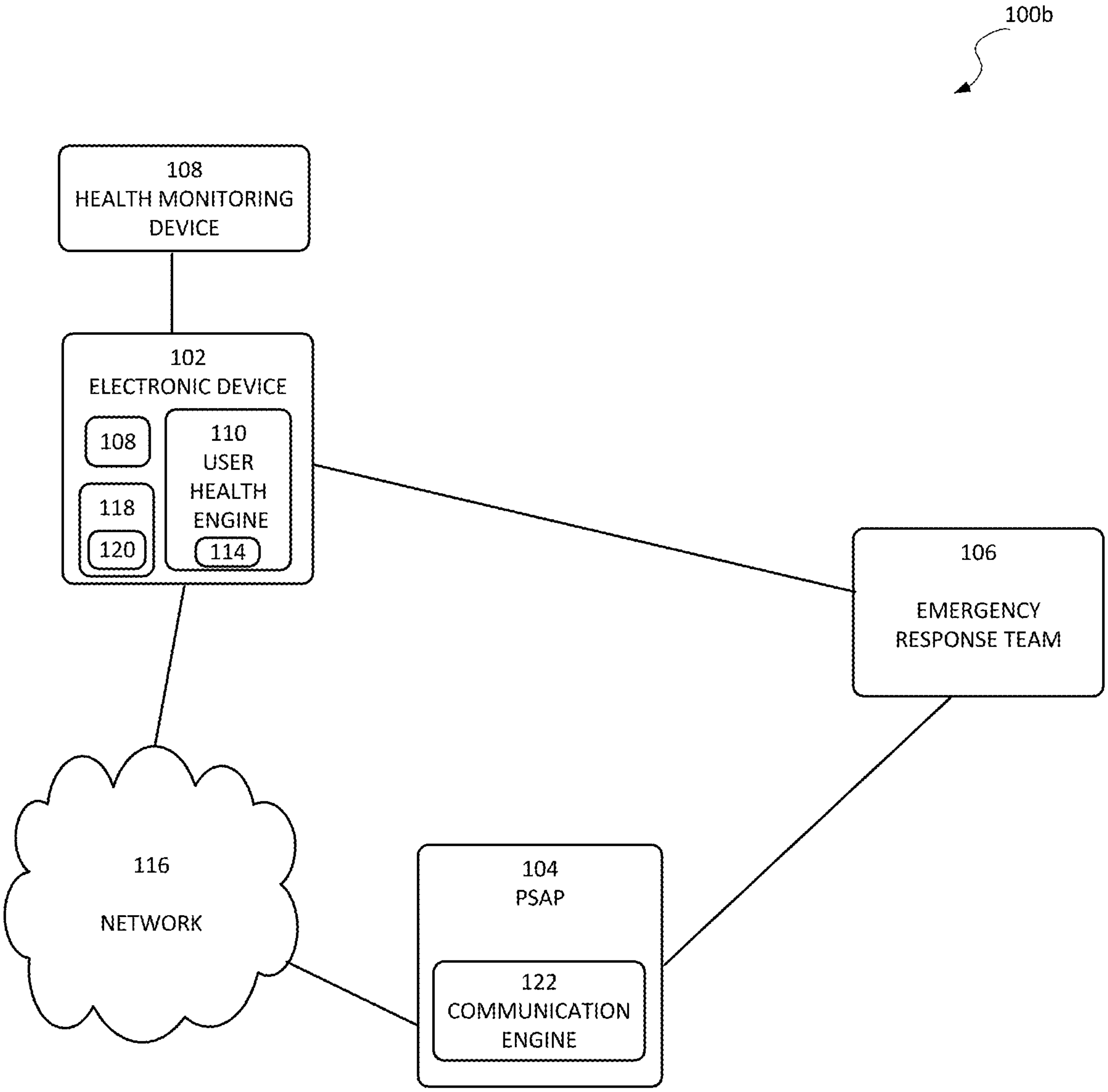
FIG. 1B is a simplified block diagram of a system to enable near real time health data communication to a PSAP and/or one or more first responders (e.g., an emergency response team), in accordance with an embodiment of the present disclosure.

Turning to FIG. 1B, FIG. 1B is simplified block diagram of a particular non-limiting health data communication system 100*b* to enable near real time health data communication to a PSAP and/or one or more first responders, in accordance with an embodiment of the present disclosure. As illustrated in FIG. 1B, the health data communication system 100*b* can include the electronic device 102, the PSAP 104, and the first responder device 106.

In an example, one or more health monitoring devices 108 are in communication with the electronic device 102. In some examples, the electronic device includes a health monitoring device 108. The electronic device 102 can include the user health engine 110 that can collect the near real time health data 120 and store the near real time health data 120 in secured memory 118 located in the electronic device 102 or some other location. In some examples, the user health engine 110 can include the health data authorization 114 that allows the user health engine 110 and the electronic device 102 to access the near real time health data 120 stored in the secured memory 118. In some examples, the health data authorization 114 can be stored in the electronic device 102.

In an illustrative example, a user of the electronic device 102 may experience a medical emergency (e.g., heart attack, fall, injury, etc.) and the user may send a communication to the PSAP 104 about the medical emergency using the network 116. The PSAP 104 can obtain the health data authorization 114, access the near real time health data 120 stored in the secured memory 118, and communicate the near real time health data 120 to the first responder device 106. By providing the first responder device 106 with the near real time health data 120, the first responder can access the real time health data 120 and gain insight into the medical emergency experienced by the user and may be better prepared to respond to the medical emergency when the first responder arrives to help the user. In some examples, the PSAP does not obtain or access the near real time health data 120 of the user and communicates the health data authorization 114 to the first responder device 106. The first responder device 106 uses the health data authorization 114 to access the near real time health data 120 for the user in the secured memory 118.

Figure 1C:
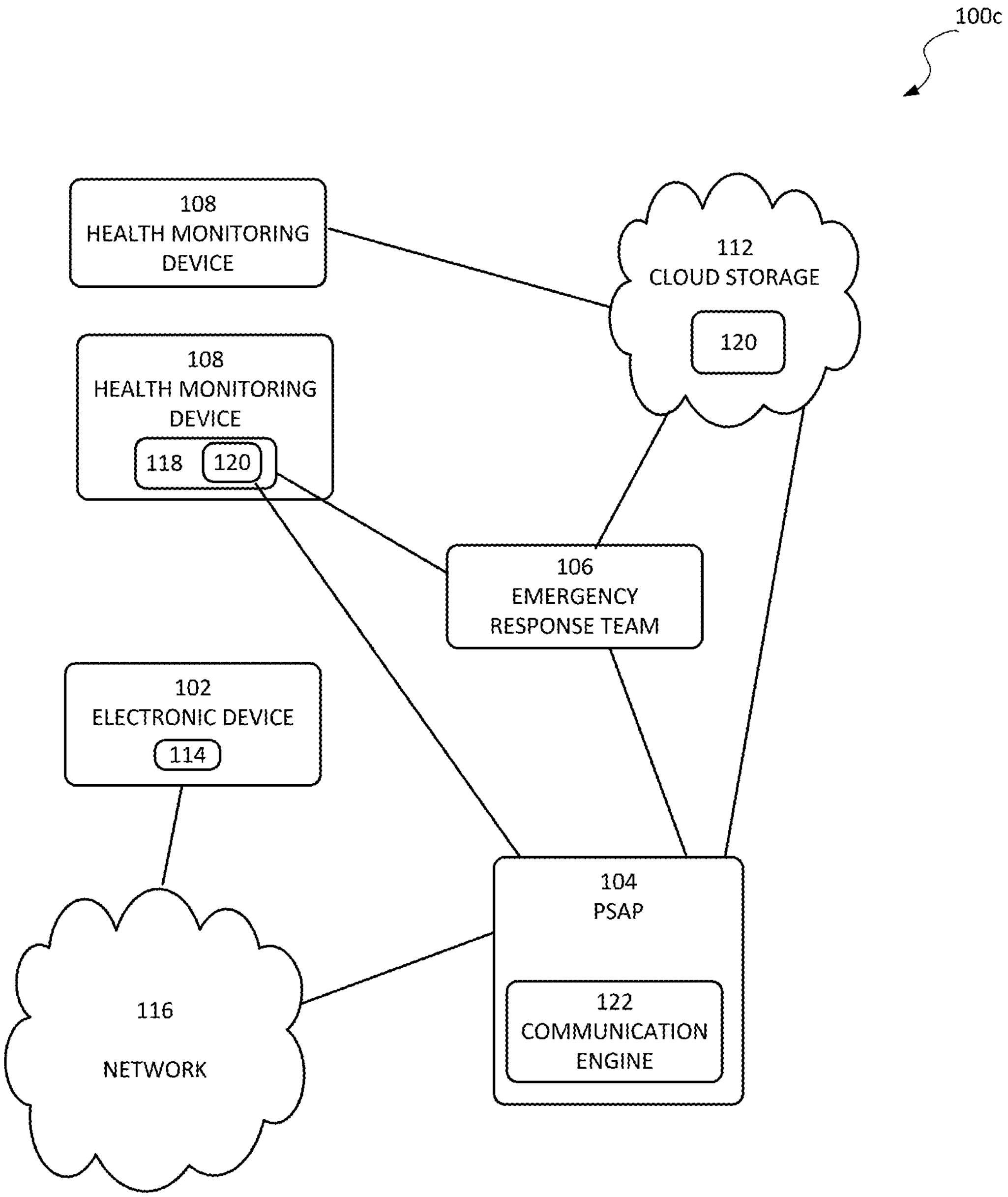
FIG. 1C is a simplified block diagram of a system to enable near real time health data communication to a PSAP and/or one or more first responders (e.g., an emergency response team), in accordance with an embodiment of the present disclosure.

Turning to FIG. 1C, FIG. 1C is simplified block diagram of a particular non-limiting health data communication system 100*c* to enable near real time health data communication to a PSAP and/or one or more first responders, in accordance with an embodiment of the present disclosure. As illustrated in FIG. 1C, the health data communication system 100*c* can include the electronic device 102, the PSAP 104, and the first responder device 106.

In an example, one or more health monitoring devices 108 store the near real time health data 120 in the cloud storage 112 or in secured memory 118 in the health monitoring device 108. The health data authorization 114 used to access the near real time health data 120 can be stored in the electronic device 102. Note that the one or more health monitoring devices 108 are not in communication with the electronic device 102.

In an illustrative example, a user of the electronic device 102 may experience a medical emergency (e.g., heart attack, fall, injury, incapacitation, etc.) and the electronic device 102 may automatically send a communication to the PSAP 104 about the medical emergency using the network 116. The PSAP 104 can obtain the health data authorization 114 from the electronic device 102, access the near real time health data 120 stored in the cloud storage 112 and/or the secured memory 118 on a health monitoring device 108, and communicate the near real time health data 120 to the first responder device 106. By providing the first responder device 106 with the near real time health data 120, the first responder can access the real time health data 120 and gain insight into the medical emergency experienced by the user and may be better prepared to respond to the medical emergency when the first responder arrives to help the user. In some examples, the PSAP does not obtain or access the near real time health data 120 of the user and communicates the health data authorization 114 to the first responder device 106. The first responder device 106 uses the health data authorization 114 to access the near real time health data 120 for the user in the cloud storage 112 and/or the secured memory 118.

It is to be understood that other embodiments and implementations may be utilized, and structural changes may be made without departing from the scope of the present disclosure. Substantial flexibility is provided by the system and method in that any suitable arrangements and configuration may be provided without departing from the teachings of the present disclosure. For purposes of illustrating certain example techniques to enable near real time communication of health data to a PSAP and/or one or more first responders, the following foundational information may be viewed as a basis from which the present disclosure may be properly explained. A number of prominent technological trends are currently afoot (e.g., more computing devices, more online services, more Internet traffic). One trend is smart health monitoring devices that can monitor one or more health indicators of a user and includes fitness trackers, smart wearables, electrocardiogram (ECG) monitors, blood pressure monitors, and biosensors. Because of privacy concerns, the health data is typically stored in a secure location that is accessible only by the user and those that are given express permission by the user to access the health data.

A PSAP, sometimes called a public safety access point, is a call center where emergency calls (like police, fire brigade, ambulance) initiated by any landline, mobile or Voice Over Internet Protocol ("VOIP") are received. When a communication is sent to a PSAP, information about the reason for the communication is gathered and if the communication is about an emergency that requires a response from a first responder, the PSAP (e.g., a trained human PSAP operator) will dispatch the necessary first responders, whether it's law enforcement, paramedics, firefighters, or other emergency services. While the first responders are traveling to the scene of the emergency, the only information the first responders know about the emergency is based on the information gathered by the PSAP. If the emergency is a medical emergency, it would be helpful if the first responders could access any near real time health data of the person with the medical emergency. What is needed is a system, an apparatus, and a method to help enable the first responders to have access to any near real time health data of a person with a medical emergency while the first responders are traveling to the scene of the medical emergency.

A system, method, apparatus, means, etc. to enable near real time communication of health data to a PSAP and/or one or more first responders can help resolve these issues (and others). In an example, one or more smart health monitoring devices (e.g., health monitoring device 108) can monitor one or more health indicators of a user and store near real time health data (e.g., near real time health data 120) for the user in a secure location (e.g., the cloud storage 112 illustrated in FIGS. 1A and 1C, the secured memory 118 illustrated in FIGS. 1B and 1C), or some other secure location. Access or an authorization (e.g., key, certificate, password, token, or some other type of authorization that will allow access the near real time health data in the secure location) to access the near real time health data in the secure location can be stored on an electronic device (e.g., phone, smart phone, tablet, laptop computer, computer, etc.) that a user may use to communicate with a PSAP. If the user has a medical emergency (e.g., heart attack, fall, injury, etc.), using the electronic device, the user can communicate with a PSAP (e.g., PSAP 104) to request help. The emergency communication for help can be a voice call, text (e.g. SMS message), video call, or some other communication to the PSAP about the medical emergency. The PSAP can communicate a health data access request to the electronic device for the authorization to allow the PSAP to access the near real time health data in the secure location. The electronic device can communicate a health data authorization to the PSAP to allow the PSAP to access the near real time health data in the secure location. The PSAP can communicate the authorization to the secure location and once the health data authorization is verified, the secure location can communicate the near real time health data to the PSAP, and the PSAP can communicate the near real time health data to one or more first responders (e.g., using the first responder device 106) that are responding to the medical emergency. As the near real time health data is updated by the health monitoring devices, the updated near real time health data can be stored in the secure location, the secure location can communicate the updated near real time health data to the PSAP, and the PSAP can communicate the updated near real time health data to the first responders. By providing the first responders with the near real time health data, the first responders can gain insight into the medical emergency experienced by the user and may be better prepared to respond to the medical emergency when the first responders arrive to help the user.

In some examples, the PSAP can communicate the near real time health data and the authorization to the first responder. The first responder can communicate the authorization to the secure location and once the health data authorization 308 is verified, the secure location can communicate the near real time health data to the first responder. As the near real time health data is updated, the updated near real time health data can be stored in the secure location and the secure location can communicate the updated near real time health data to the first responder.

In some examples, the PSAP does not access the near real time health data and can communicate the health data authorization to the first responder to allow the first responder to access the near real time health data in the secure location. In some examples, the authorization to access the near real time health data is sent with the communication to the PSAP. For example, if the user has been knocked unconscious, is suffering from dangerously low blood sugar, is having a heart attack, or is otherwise incapacitated or potentially suffering a life-threatening medical emergency, the authorization to access the health data stored in the secure location can be communicated to the PSAP along with the communication to the PSAP regarding the medical emergency. In some examples, the user may have pre-programmed or pre-provisioned the electronic device that sent the emergency communication to the PSAP regarding the medical emergency so the authorization to access the health data is automatically communicated along with the communication regarding the medical emergency.

Figure 2:
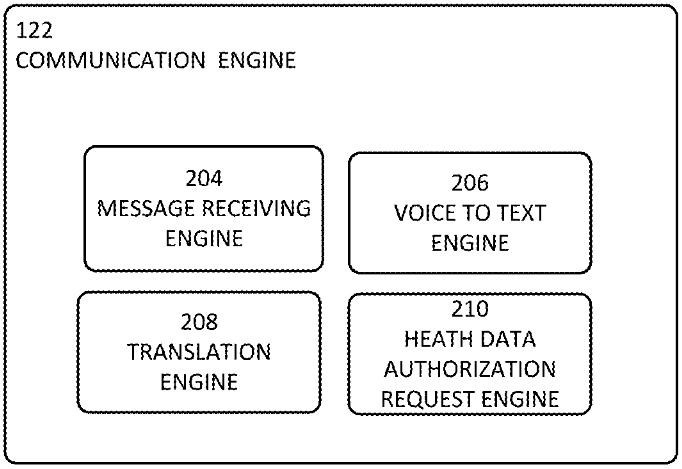
FIG. 2 is a simplified block diagram of a particular implementation of a communication engine to help enable near real time health data communication to a PSAP and/or one or more first responders, in accordance with an embodiment of the present disclosure.

Turning to FIG. 2, FIG. 2 is a simplified block diagram illustrating example details of a particular non-limiting implementation of the communication engine 122. The communication engine 122 can include a message receiving engine 204, a voice to text engine 206, a translation engine 208, and a health data authorization request engine 210.

The message receiving engine 204 receives text messages and audio communication or voice messages. The voice to text engine 206 converts audio communication and voice messages into text. The translation engine 208 translates received text messages and the text of audio communication and voice message into a preferred language of the PSAP operator. For example, if the preferred language of the PSAP operator is English, then the translation engine will convert received text messages and the text of audio communication into English. The translation engine 208 can also translate any scripts or communications with the user of the electronic device 102 that originated the communication into a preferred language of the user of the electronic device 102. The health data authorization request engine 210 is configured to send a request for the health data authorization 114, to access the near real time health data 120 for the user in the secured memory 118, communicate the near real time health data 120 to the first responder device 106, and/or communicate the health data authorization 114 to the first responder device 106.

Figure 3:
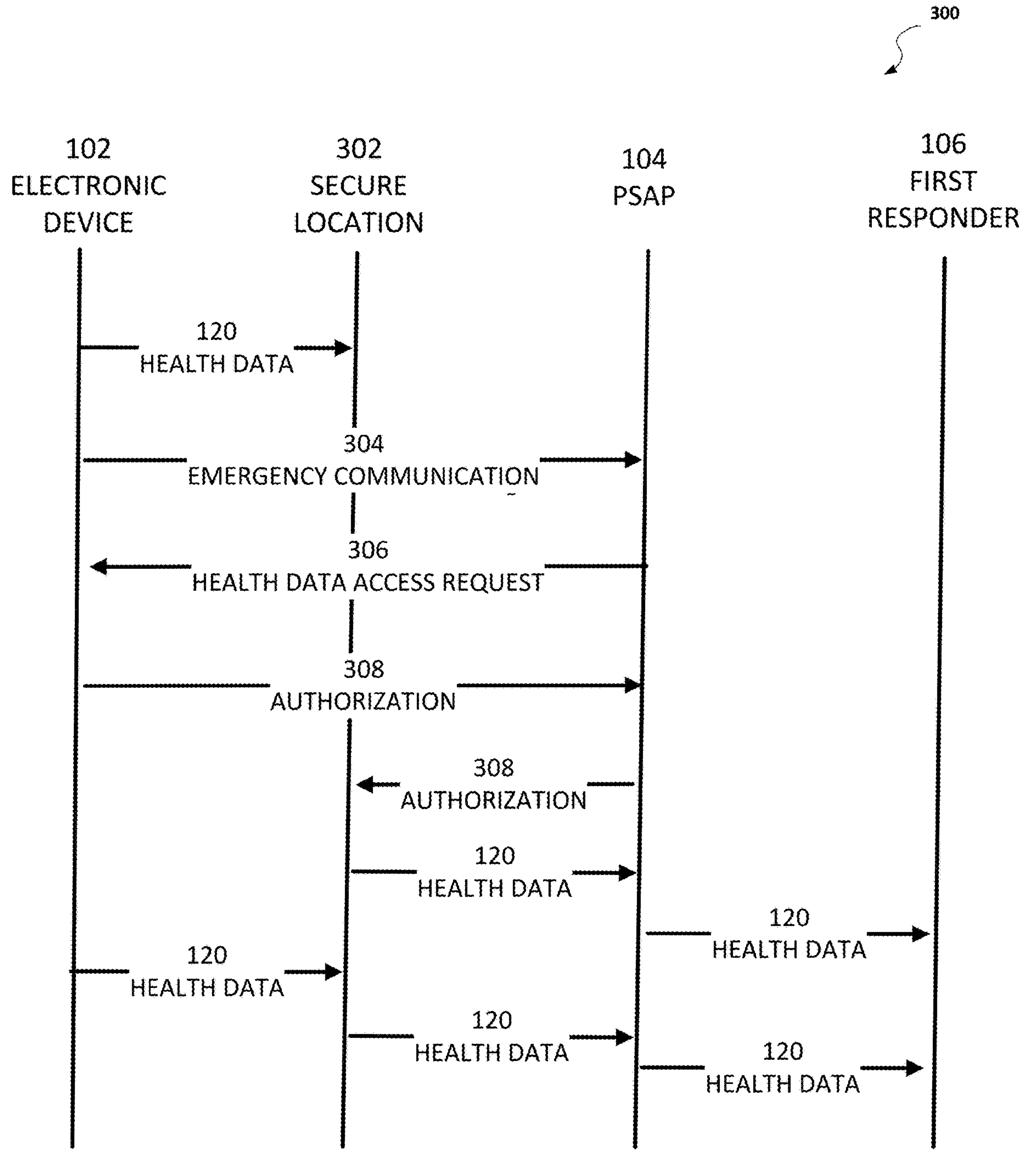
FIG. 3 is a simplified timing diagram of a particular implementation to help enable near real time health data communication to a PSAP and/or one or more first responders, in accordance with an embodiment of the present disclosure.

Turning to FIG. 3, FIG. 3 is a simplified timing diagram 300 illustrating specific example details of a system, apparatus, and method to help enable near real time communication of health data to a PSAP and/or one or more first responders. In an illustrative example, the electronic device 102 can send near real time health data 120 to a secure location 302. The near real time health data 120 is near real time health data for a user of the electronic device 102 and includes data from the one or more health monitoring devices 108 (illustrated in FIGS. 1A-1C). The secure location 302 can be the cloud storage 112 (illustrated in FIGS. 1A and 1C), the secured memory 118 (illustrated in FIGS. 1B and 1C), or some other secure location. In some examples, one or more of the health monitoring devices 108 sends the health data for the user to the secure location 302.

If the user has a medical emergency (e.g., heart attack, fall, injury, etc.), the user can communicate an emergency communication 304 to the PSAP 104 to request help. The emergency communication 304 can be a voice call, text (e.g. SMS message), video call, or some other communication to the PSAP 104 about the medical emergency. The PSAP 104 can communicate a health data access request 306 to the electronic device 102 to allow the PSAP 104 to access the near real time health data 120 in the secure location 302. The electronic device 102 can communicate a health data authorization 308 to the PSAP 104 to allow the PSAP 104 to access the near real time health data 120 in the secure location 302. The health data authorization 308 can be a key, certificate, password, token, or some other type of authorization that will allow the PSAP 104 to access the near real time health data 120 in the secure location 302. The PSAP 104 can communicate the health data authorization 308 to the secure location 302 and once the health data authorization 308 is verified, the secure location 302 can communicate the near real time health data 120 to the PSAP 104, and the PSAP 104 can communicate the near real time health data 120 to the first responder device 106. As the near real time health data 120 is updated, the electronic device 102 can communicate the updated near real time health data 120 to the secure location 302, the secure location can communicate the updated near real time health data 120 to the PSAP 104, and the PSAP 104 can communicate the updated near real time health data 120 to the first responder device 106. By providing the first responder device 106 with the near real time near real time health data 120, the first responder can access the real time health data 120 and gain insight into the medical emergency experienced by the user and may be better prepared to respond to the medical emergency when the first responder arrives to help the user.

Figure 4:
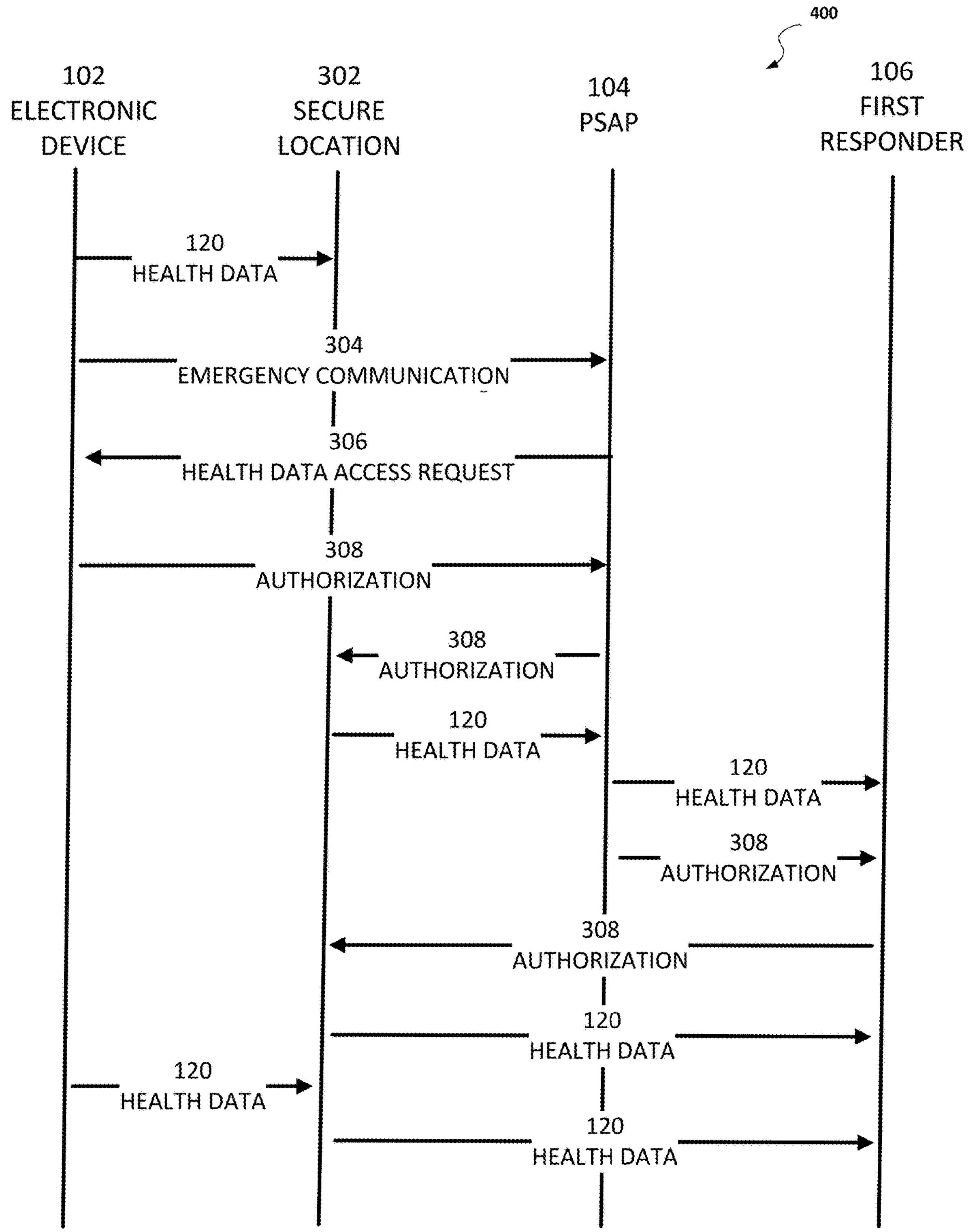
FIG. 4 is a simplified timing diagram of a particular implementation to help enable near real time health data communication to a PSAP and/or one or more first responders, in accordance with an embodiment of the present disclosure.

Turning to FIG. 4, FIG. 4 is a simplified timing diagram 400 illustrating specific example details of a system, apparatus, and method to help enable near real time communication of health data to a PSAP and/or one or more first responders. In an illustrative example, the electronic device 102 can send near real time health data 120 to the secure location 302. The near real time health data 120 is near real time health data for a user of the electronic device 102 and includes data from the one or more health monitoring devices 108 (illustrated in FIGS. 1A-1C). The secure location 302 can be the cloud storage 112 (illustrated in FIGS. 1A and 1C), the secured memory 118 (illustrated in FIGS. 1B and 1C), or some other secure location. In some examples, one or more of the health monitoring devices 108 sends the health data for the user to the secure location 302.

If the user has a medical emergency (e.g., heart attack, fall, injury, etc.), the user can communicate an emergency communication 304 to the PSAP 104 to request help. The emergency communication 304 can be a voice call, text (e.g. SMS message), video call, or some other communication to the PSAP 104 about the medical emergency. The PSAP 104 can communicate the health data access request 306 to the electronic device 102 to allow the PSAP 104 to access the near real time health data 120 in the secure location 302. The electronic device 102 can communicate a health data authorization 308 to the PSAP 104 to allow the PSAP 104 to access the near real time health data 120 in the secure location 302. The health data authorization 308 can be a key, certificate, password, or some other type of authorization that will allow the PSAP 104 to access the near real time health data 120 in the secure location 302. The PSAP 104 can communicate the health data authorization 308 to the secure location 302 and once the health data authorization 308 is verified, the secure location 302 can communicate the near real time health data 120 to the PSAP 104, and the PSAP 104 can communicate the near real time health data 120 and the health data authorization 308 to the first responder device 106. The first responder device 106 can communicate the health data authorization 308 to the secure location 302 and once the health data authorization 308 is verified, the secure location 302 can communicate the near real time health data 120 to the first responder device 106. As the near real time health data 120 is updated, the electronic device 102 can communicate the updated near real time health data 120 to the secure location 302 and the secure location can communicate the updated near real time health data 120 to the first responder device 106. By providing the first responder device 106 with the near real time near real time health data 120, the first responder can access the real time health data 120 and gain insight into the medical emergency experienced by the user and may be better prepared to respond to the medical emergency when the first responder arrives to help the user.

Figure 5:
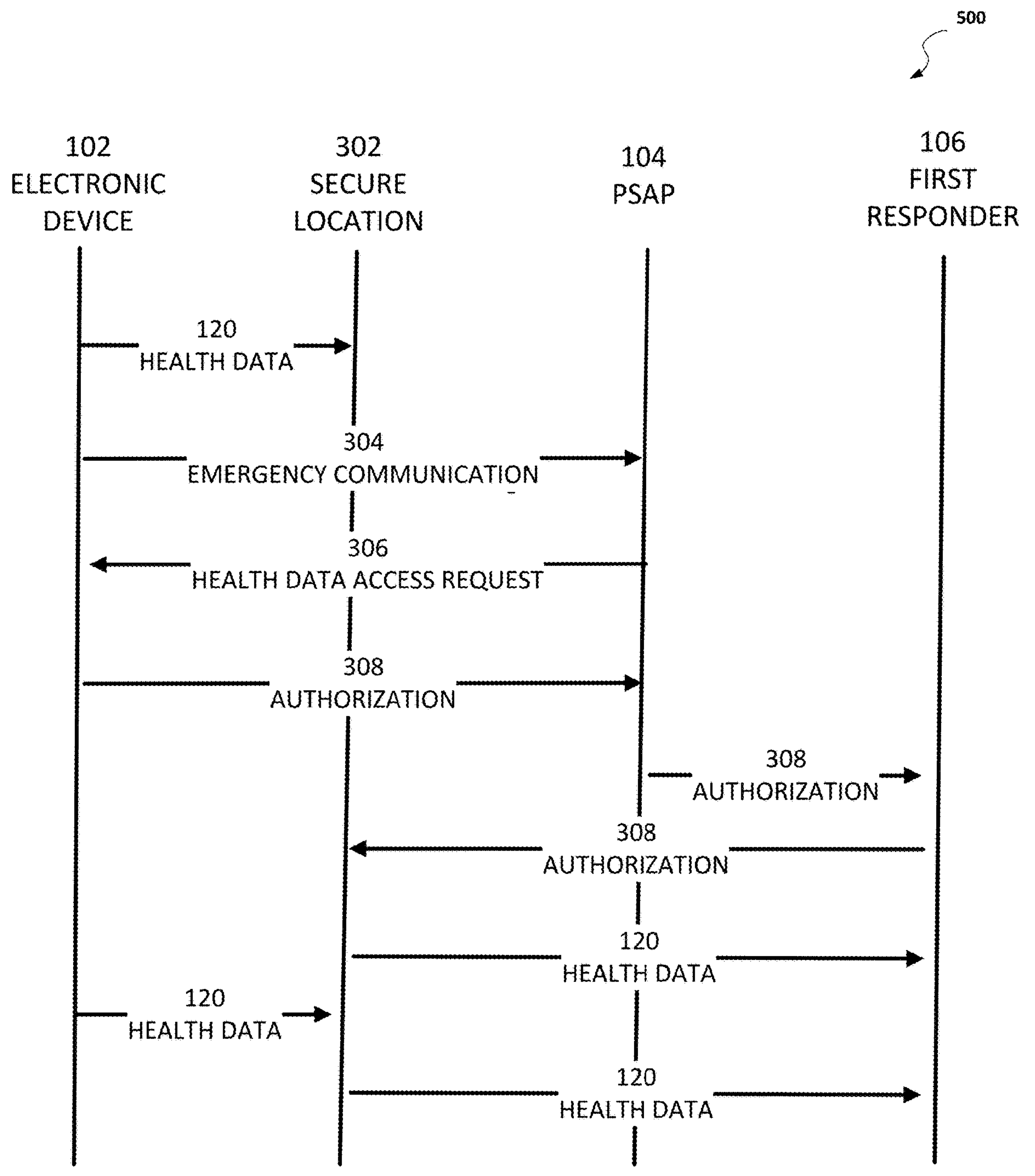
FIG. 5 is a simplified timing diagram of a particular implementation to help enable near real time health data communication to a PSAP and/or one or more first responders, in accordance with an embodiment of the present disclosure.

Turning to FIG. 5, FIG. 5 is a simplified timing diagram 500 illustrating specific example details of a system, apparatus, and method to help enable near real time communication of health data to a PSAP and/or one or more first responders. In an illustrative example, the electronic device 102 can send near real time health data 120 to the secure location 302. The near real time health data 120 is near real time health data for a user of the electronic device 102 and includes data from the one or more health monitoring devices 108 (illustrated in FIGS. 1A-1C). The secure location 302 can be the cloud storage 112 (illustrated in FIGS. 1A and 1C), the secured memory 118 (illustrated in FIGS. 1B and 1C), or some other secure location. In some examples, one or more of the health monitoring devices 108 sends the health data for the user to the secure location 302.

If the user has a medical emergency (e.g., heart attack, fall, injury, etc.), the user can communicate an emergency communication 304 to the PSAP 104 to request help. The emergency communication 304 can be a voice call, text (e.g. SMS message), video call, or some other communication to the PSAP 104 about the medical emergency. The PSAP 104 can communicate the health data access request 306 to the electronic device 102. The electronic device 102 can communicate a health data authorization 308 to the PSAP 104 and the PSAP 104 can communicate the health data authorization 308 to the first responder device 106 to allow the first responder device 106 to access the near real time health data 120 in the secure location 302. The health data authorization 308 can be a key, certificate, password, or some other type of authorization that will allow the PSAP 104 to access the near real time health data 120 in the secure location 302. The first responder device 106 can communicate the health data authorization 308 to the secure location 302 and once the health data authorization 308 is verified, the secure location 302 can communicate the near real time health data 120 to the first responder device 106. As the near real time health data 120 is updated, the electronic device 102 can communicate the updated near real time health data 120 to the secure location 302 and the secure location can communicate the updated near real time health data 120 to the first responder device 106. By providing the first responder device 106 with the near real time near real time health data 120, the first responder can access the real time health data 120 and gain insight into the medical emergency experienced by the user and may be better prepared to respond to the medical emergency when the first responder arrives to help the user.

Figure 6:
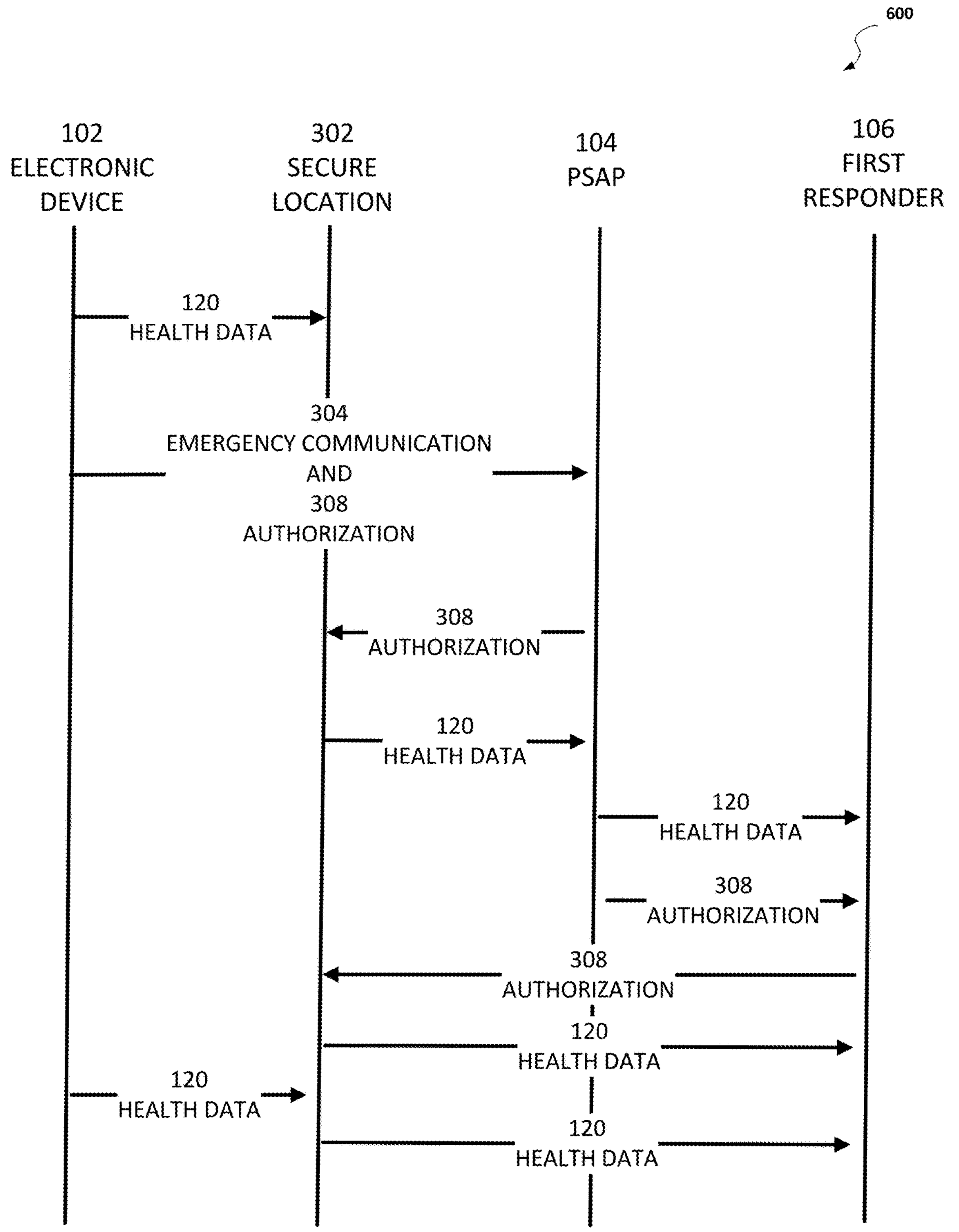
FIG. 6 is a simplified timing diagram of a particular implementation to help enable near real time health data communication to a PSAP and/or one or more first responders, in accordance with an embodiment of the present disclosure.

Turning to FIG. 6, FIG. 6 is a simplified timing diagram 600 illustrating specific example details of a system, apparatus, and method to help enable near real time communication of health data to a PSAP and/or one or more first responders. In an illustrative example, the electronic device 102 can send near real time health data 120 to the secure location 302. The near real time health data 120 is near real time health data for a user of the electronic device 102 and includes data from the one or more health monitoring devices 108 (illustrated in FIGS. 1A-1C). The secure location 302 can be the cloud storage 112 (illustrated in FIGS. 1A and 1C), the secured memory 118 (illustrated in FIGS. 1B and 1C), or some other secure location. In some examples, one or more of the health monitoring devices 108 sends the health data for the user to the secure location 302.

If the user has a medical emergency (e.g., heart attack, fall, injury, etc.), the user can communicate an emergency communication 304 and the health data authorization 308 to the PSAP 104 to request help. In some examples, the electronic device 102 is pre-programmed or pre-provisioned by the user to automatically send the health data authorization 308 to the PSAP 104 when the emergency communication is sent to the PSAP 104. The emergency communication 304 can be a voice call, text (e.g. SMS message), video call, or some other communication to the PSAP 104 about the medical emergency. The health data authorization 308 can be a key, certificate, password, or some other type of authorization that will allow the PSAP 104 to access the near real time health data 120 in the secure location 302. The PSAP 104 can communicate the health data authorization 308 to the secure location 302 and once the health data authorization 308 is verified, the secure location 302 can communicate the near real time health data 120 to the PSAP 104, and the PSAP 104 can communicate the near real time health data 120 and the health data authorization 308 to the first responder device 106. The first responder device 106 can communicate the health data authorization 308 to the secure location 302 and once the health data authorization 308 is verified, the secure location 302 can communicate the near real time health data 120 to the first responder device 106. As the near real time health data 120 is updated, the electronic device 102 can communicate the updated near real time health data 120 to the secure location 302 and the secure location can communicate the updated near real time health data 120 to the first responder device 106. By providing the first responder device 106 with the near real time near real time health data 120, the first responder can access the real time health data 120 and gain insight into the medical emergency experienced by the user and may be better prepared to respond to the medical emergency when the first responder arrives to help the user.

Figure 7:
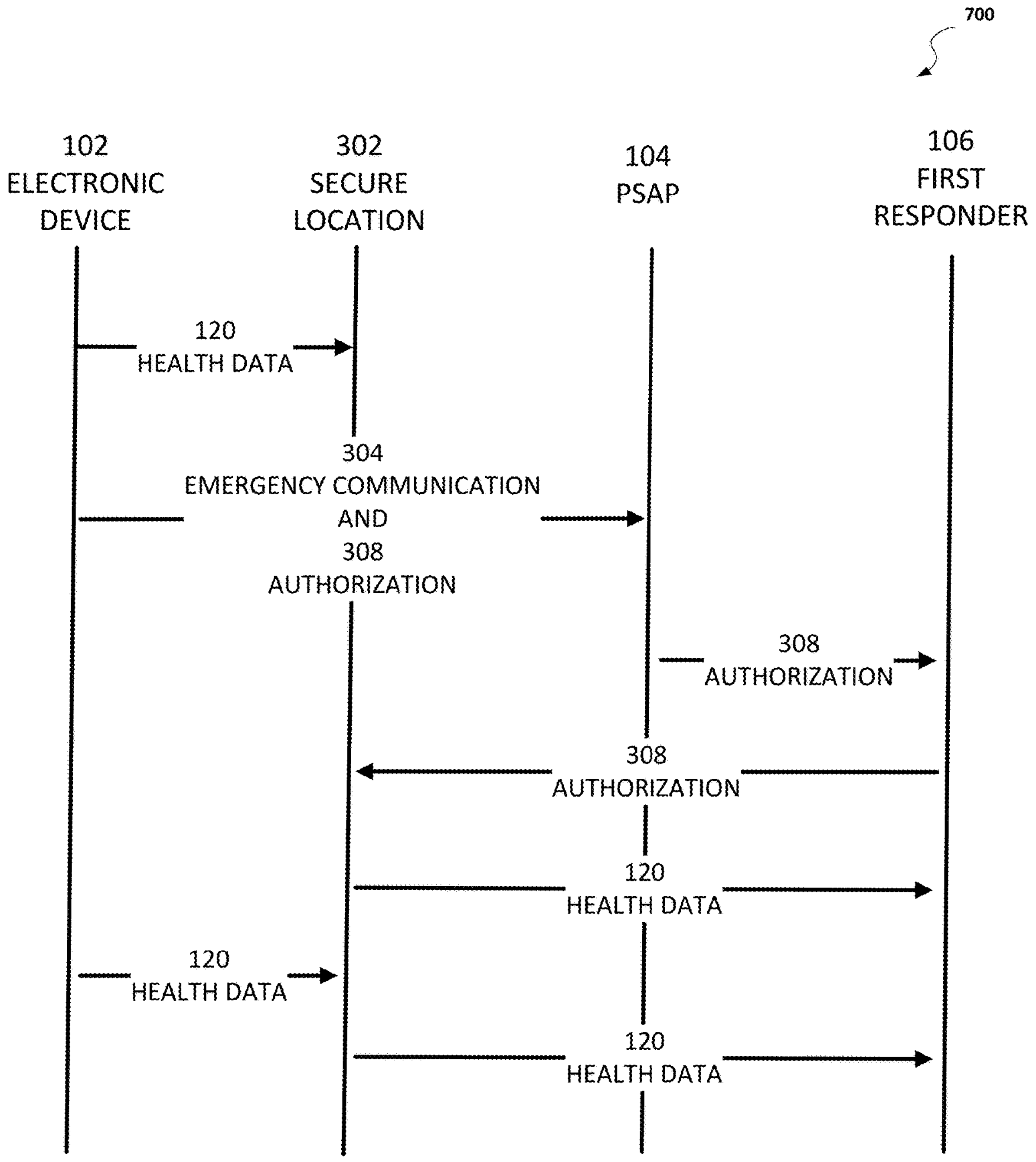
FIG. 7 is a simplified timing diagram of a particular implementation to help enable near real time health data communication to a PSAP and/or one or more first responders, in accordance with an embodiment of the present disclosure.

Turning to FIG. 7, FIG. 7 is a simplified timing diagram 700 illustrating specific example details of a system, apparatus, and method to help enable near real time communication of health data to a PSAP and/or one or more first responders. In an illustrative example, the electronic device 102 can send near real time health data 120 to the secure location 302. The near real time health data 120 is near real time health data for a user of the electronic device 102 and includes data from the one or more health monitoring devices 108 (illustrated in FIGS. 1A-1C). The secure location 302 can be the cloud storage 112 (illustrated in FIGS. 1A and 1C), the secured memory 118 (illustrated in FIGS. 1B and 1C), or some other secure location. In some examples, one or more of the health monitoring devices 108 sends the health data for the user to the secure location 302.

If the user has a medical emergency (e.g., heart attack, fall, injury, etc.), the user can communicate an emergency communication 304 and the health data authorization 308 to the PSAP 104 to request help. In some examples, the electronic device 102 is pre-programmed or pre-provisioned by the user to automatically send the health data authorization 308 to the PSAP 104 when the emergency communication is sent to the PSAP 104. The emergency communication 304 can be a voice call, text (e.g. SMS message), video call, or some other communication to the PSAP 104 about the medical emergency. The health data authorization 308 can be a key, certificate, password, or some other type of authorization that will allow the PSAP 104 to access the near real time health data 120 in the secure location 302. The PSAP 104 can communicate the health data authorization 308 to the first responder device 106. The first responder device 106 can communicate the health data authorization 308 to the secure location 302 and once the health data authorization 308 is verified, the secure location 302 can communicate the near real time health data 120 to the first responder device 106. As the near real time health data 120 is updated, the electronic device 102 can communicate the updated near real time health data 120 to the secure location 302 and the secure location can communicate the updated near real time health data 120 to the first responder device 106. By providing the first responder device 106 with the near real time near real time health data 120, the first responder can access the real time health data 120 and gain insight into the medical emergency experienced by the user and may be better prepared to respond to the medical emergency when the first responder arrives to help the user.

Figure 8:
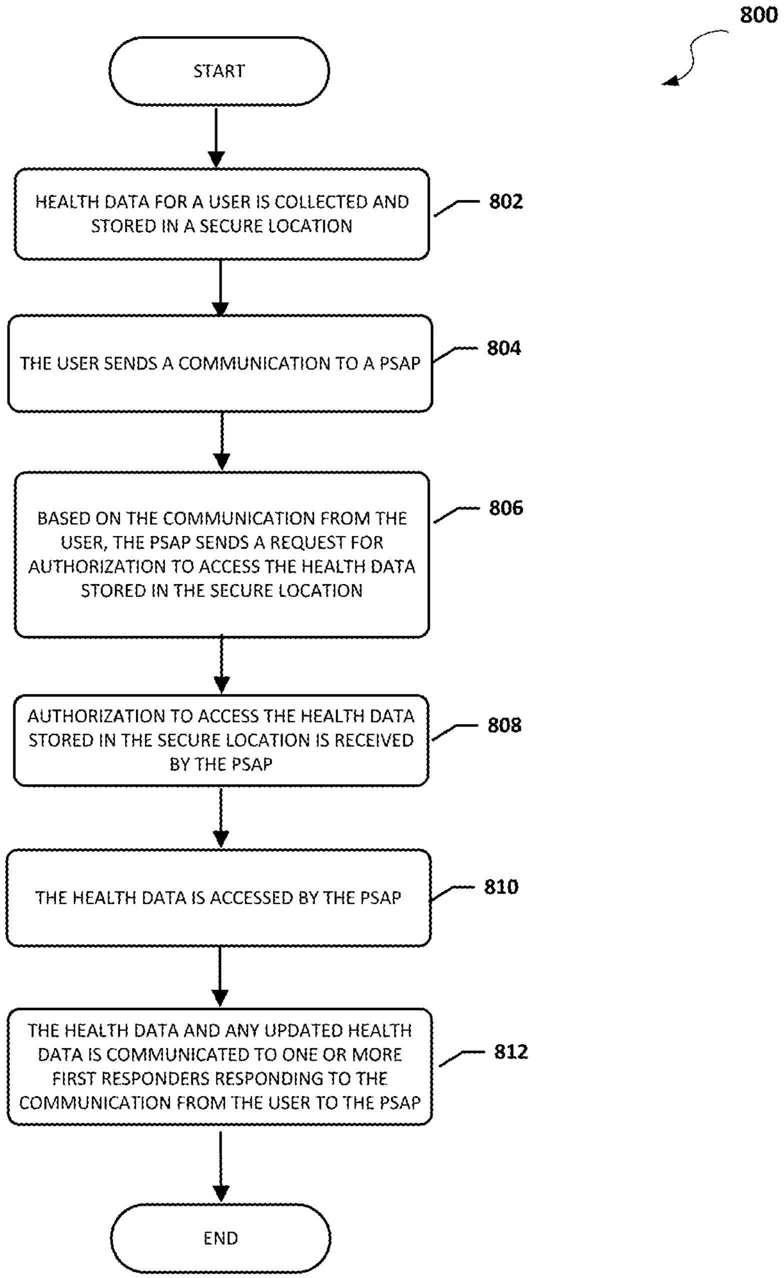
FIG. 8 is a simplified flowchart illustrating potential operations to help enable near real time health data communication to a PSAP and/or one or more first responders, in accordance with an embodiment of the present disclosure.

Turning to FIG. 8, FIG. 8 is example flowchart illustrating possible operations of a flow 800 that may be associated with potential operations to help enable near real time communication of health data to a PSAP and/or one or more first responders, in accordance with an embodiment of the present disclosure. Specifically, in some examples, one or more operations of flow 800 may be performed by the PSAP 104, the communication engine 122, and/or the health data authorization request engine 210. At 802, health data for a user is collected and stored in a secure location. For example, one or more health monitoring devices 108 can collect health data for a user and the health data 120 can be stored in the secure location 302 (e.g., the cloud storage 112, the secured memory 118, or some other secure location). At 804, the user sends a communication to a PSAP. For example, the communication may be a voice call, text (e.g. SMS message), video call, or some other communication from the electronic device 102 to the PSAP 104 about a medical emergency the user is experiencing. At 806, based on the communication from the user, the PSAP sends a request for authorization to access the health data 120 stored in the secure location. For example, if a PSAP operator dispatches first responders to the user to help the user with the medical emergency, the PSAP 104 can communicate a request to the user for the authorization to access the health data 120 stored in the secure location 302. At 808, authorization to access the health data stored in the secure location is received by the PSAP. For example, the PSAP 104 can receive a key, certificate, password, token, or some other type of authorization (e.g., health data authorization 308) that will allow the PSAP 104 to access the health data 120 in the secure location 302. At 810, the health data is access by the PSAP. For example, the PSAP 104 can use the authorization to access the health data 120 in the secure location 302. At 812, the health data and any updated health data is communication to one or more first responders responding to the communication from the user to the PSAP. For example, the PSAP 104 can communicate the health data 120 and any updated health data 120 to the first responder device 106.

Figure 9:
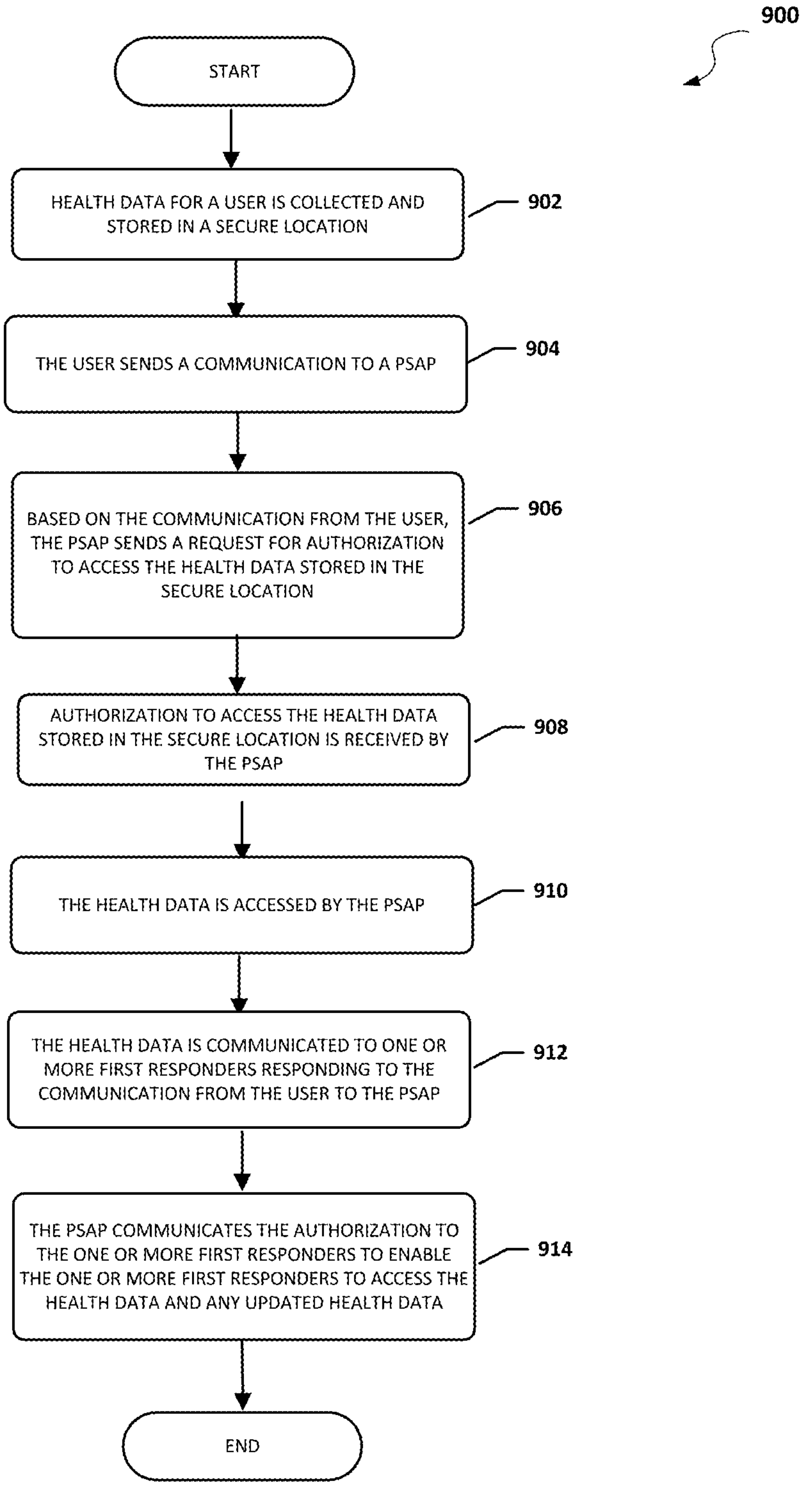
FIG. 9 is a simplified flowchart illustrating potential operations to help enable near real time health data communication to a PSAP and/or one or more first responders, in accordance with an embodiment of the present disclosure.

Turning to FIG. 9, FIG. 9 is example flowchart illustrating possible operations of a flow 900 that may be associated with potential operations to help enable near real time communication of health data to a PSAP and/or one or more first responders, in accordance with an embodiment of the present disclosure. Specifically, in some examples, one or more operations of flow 900 may be performed by the PSAP 104, the communication engine 122, and/or the health data authorization request engine 210. At 902, health data for a user is collected and stored in a secure location. For example, one or more health monitoring devices 108 can collect health data for a user and the health data 120 can be stored in the secure location 302 (e.g., the cloud storage 112, the secured memory 118, or some other secure location). At 904, the user sends a communication to a PSAP. For example, the communication may be a voice call, text (e.g. SMS message), video call, or some other communication from the electronic device 102 to the PSAP 104 about a medical emergency the user is experiencing. At 906, based on the communication from the user, the PSAP sends a request for authorization to access the health data stored in the secure location. For example, if a PSAP operator dispatches first responders to the user to help the user with the medical emergency, the PSAP 104 can communicate a request to the user for the authorization to access the health data 120 stored in the secure location 302. At 908, authorization to access the health data stored in the secure location is received by the PSAP. For example, the PSAP 104 can receive a key, certificate, password, token, or some other type of authorization (e.g., health data authorization 308) that will allow the PSAP 104 to access the health data 120 in the secure location 302. At 910, the health data is access by the PSAP. For example, the PSAP 104 can use the authorization to access the health data 120 in the secure location 302. At 912, the health data is communication to first responders responding to the communication from the user to the PSAP. For example, the PSAP 104 can communicate the health data 120 to the first responder device 106. At 914, the PSAP communicates the authorization to the one or more first responders to enable the one or more first responders to access the health data and any updated health data. For example, the PSAP 104 can communication the authorization to access the health data 120 stored in the secure location 302 to first responder device 106 and the first responder device 106 can use the authorization to access the health data 120 and any updated health data 120 stored in the secure location 302.

Figure 10:
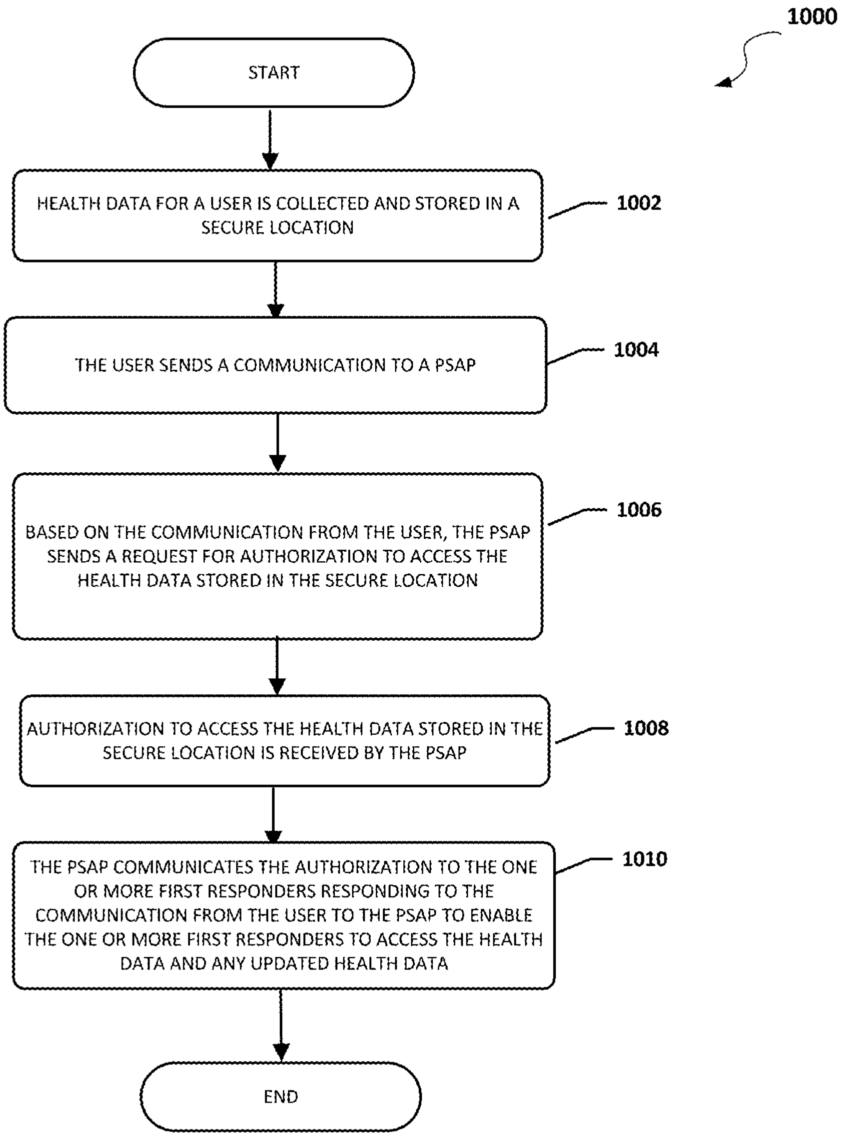
FIG. 10 is a simplified flowchart illustrating potential operations to help enable near real time health data communication to a PSAP and/or one or more first responders, in accordance with an embodiment of the present disclosure.

Turning to FIG. 10, FIG. 10 is example flowchart illustrating possible operations of a flow 1000 that may be associated with potential operations to help enable near real time communication of health data to a PSAP and/or one or more first responders, in accordance with an embodiment of the present disclosure. Specifically, in some examples, one or more operations of flow 1000 may be performed by the PSAP 104, the communication engine 122, and/or the health data authorization request engine 210. At 1002, health data for a user is collected and stored in a secure location. For example, one or more health monitoring devices 108 can collect health data for a user and the health data 120 can be stored in the secure location 302 (e.g., the cloud storage 112, the secured memory 118, or some other secure location). At 1004, the user sends a communication to a PSAP. For example, the communication may be a voice call, text (e.g. SMS message), video call, or some other communication from the electronic device 102 to the PSAP 104 about a medical emergency the user is experiencing. At 1006, based on the communication from the user, the PSAP sends a request for authorization to access the health data stored in the secure location. For example, if a PSAP operator dispatches first responders to the user to help the user with the medical emergency, the PSAP 104 can communicate a request to the user for the authorization to access the health data 120 stored in the secure location 302. At 1008, authorization to access the health data stored in the secure location is received by the PSAP. For example, the PSAP 104 can receive a key, certificate, password, token, or some other type of authorization (e.g., health data authorization 308) that will allow the PSAP 104 to access the health data 120 in the secure location 302. At 1010, the PSAP communicates the authorization to the one or more first responders responding to the communication from the user to the PSAP to enable the one or more first responders to access the health data and any updated health data. For example, the PSAP 104 can communication the authorization to access the health data 120 stored in the secure location 302 to first responder device 106 and the first responder device 106 can use the authorization to access the health data 120 and any updated health data 120 stored in the secure location 302.

Figure 11:
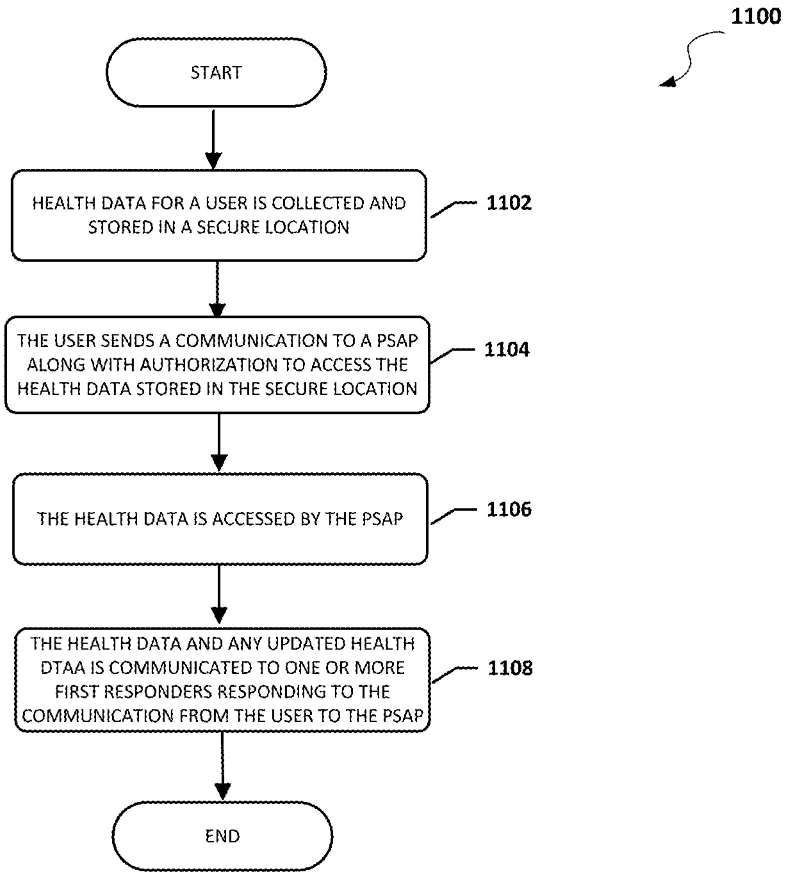
FIG. 11 is a simplified flowchart illustrating potential operations to help enable near real time health data communication to a PSAP and/or one or more first responders, in accordance with an embodiment of the present disclosure.

Turning to FIG. 11, FIG. 11 is example flowchart illustrating possible operations of a flow 1100 that may be associated with potential operations to help enable near real time communication of health data to a PSAP and/or one or more first responders, in accordance with an embodiment of the present disclosure. Specifically, in some examples, one or more operations of flow 1100 may be performed by the PSAP 104, the communication engine 122, and/or the health data authorization request engine 210. At 1102, health data for a user is collected and stored in a secure location. For example, one or more health monitoring devices 108 can collect health data for a user and the health data 120 can be stored in the secure location 302 (e.g., the cloud storage 112, the secured memory 118, or some other secure location). At 1104, the user sends a communication to a PSAP along with authorization to access the health data stored in the secure location. For example, the communication may be a voice call, text (e.g. SMS message), video call, or some other communication from the electronic device 102 to the PSAP 104 about a medical emergency the user is experiencing. The authorization (e.g., health data authorization 308) may be a key, certificate, password, token, or some other type of authorization that will allow the PSAP 104 to access the health data 120 in the secure location 302. In some examples, the user may have pre-programmed or pre-provisioned the electronic device 102 to automatically include the authorization with the communication to the PSAP 104. At 1106, the health data is accessed by the PSAP. For example, the PSAP 104 can use the authorization to access the health data 120 in the secure location 302. At 1108, the health data and any updated health data is communication to first responders responding to the communication from the user to the PSAP. For example, the PSAP 104 can communicate the health data 120 and any updated health data 120 to the first responder device 106.

Figure 12:
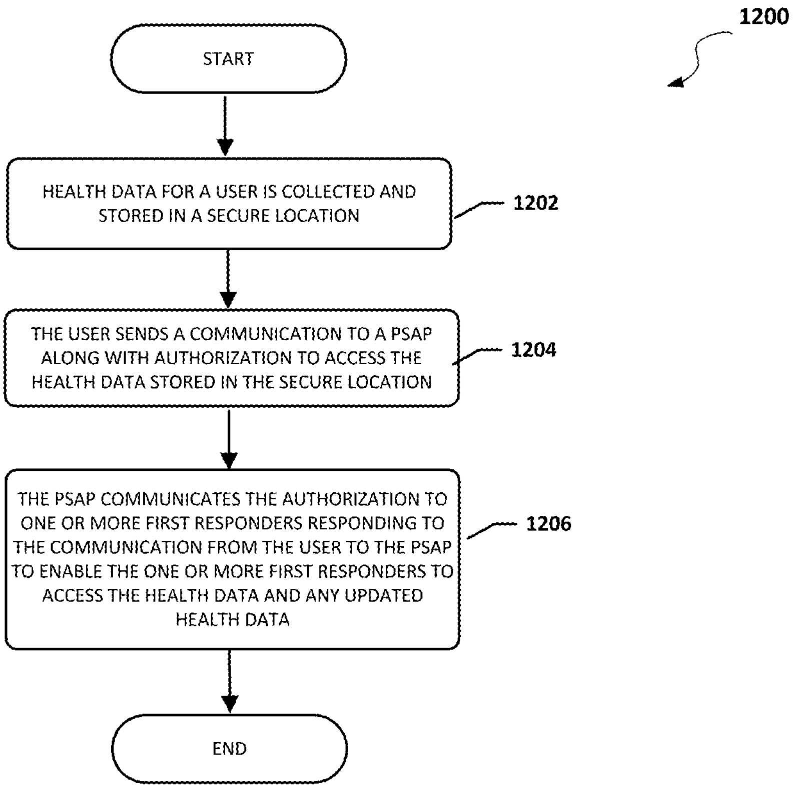
FIG. 12 is a simplified flowchart illustrating potential operations to help enable near real time health data communication to a PSAP and/or one or more first responders, in accordance with an embodiment of the present disclosure.

Turning to FIG. 12, FIG. 12 is example flowchart illustrating possible operations of a flow 1200 that may be associated with potential operations to help enable near real time communication of health data to a PSAP and/or one or more first responders, in accordance with an embodiment of the present disclosure. Specifically, in some examples, one or more operations of flow 1200 may be performed by the PSAP 104, the communication engine 122, and/or the health data authorization request engine 210. At 1202, health data for a user is collected and stored in a secure location. For example, one or more health monitoring devices 108 can collect health data for a user and the health data 120 can be stored in the secure location 302 (e.g., the cloud storage 112, the secured memory 118, or some other secure location). At 1204, the user sends a communication to a PSAP along with authorization to access the health data stored in the secure location. For example, the communication may be a voice call, text (e.g. SMS message), video call, or some other communication from the electronic device 102 to the PSAP 104 about a medical emergency the user is experiencing. The authorization (e.g., health data authorization 308) may be a key, certificate, password, token, or some other type of authorization that will allow the PSAP 104 to access the health data 120 in the secure location 302. In some examples, the user may have pre-programmed or pre-provisioned the electronic device 102 to automatically include the authorization with the communication to the PSAP 104. In other examples, if the user has been knocked unconscious, is suffering from dangerously low blood sugar, is having a heart attack, or is otherwise incapacitated or potentially suffering a life-threatening medical emergency, the electronic device 102 can sent an alert to the PSAP regarding the medical emergency along with the authorization to access the health data 120 stored in the secure location 302. At 1206, the PSAP communicates the authorization to first responders responding to the communication from the user to the PSAP to enable the first responders to access the health data and any updated health data. For example, the PSAP 104 can communication the authorization to access the health data 120 stored in the secure location 302 to the first responder device 106 and the first responder device 106 can use the authorization to access the health data 120 and any updated health data 120 stored in the secure location 302.

Figure 13:
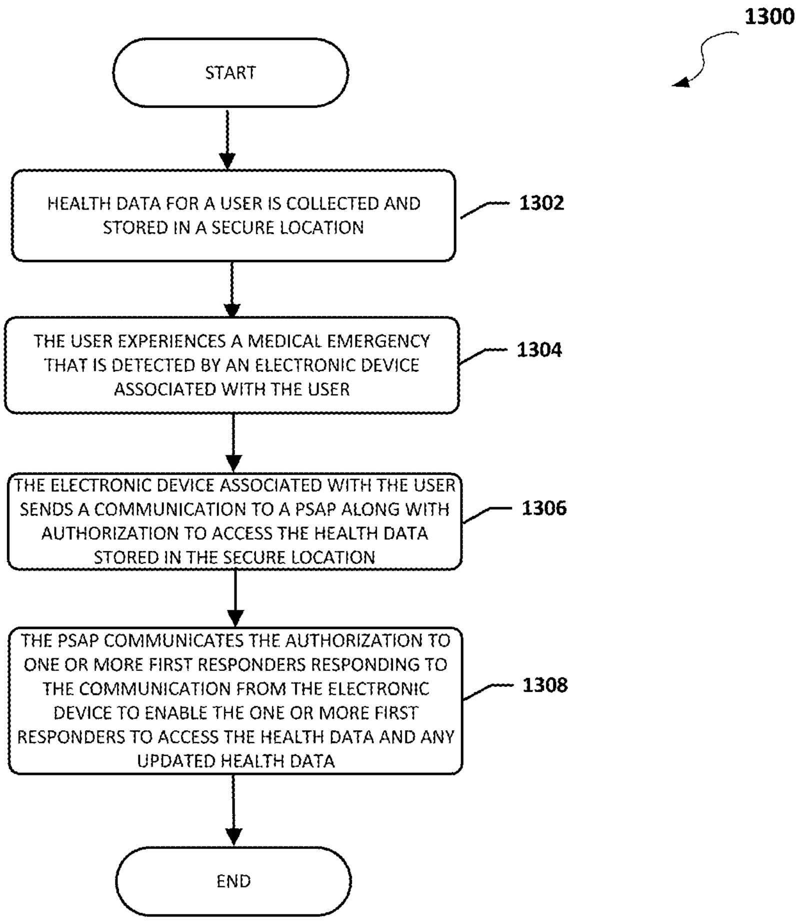
FIG. 13 is a simplified flowchart illustrating potential operations to help enable near real time health data communication to a PSAP and/or one or more first responders, in accordance with an embodiment of the present disclosure.

Turning to FIG. 13, FIG. 13 is example flowchart illustrating possible operations of a flow 1300 that may be associated with potential operations to help enable near real time communication of health data to a PSAP and/or one or more first responders, in accordance with an embodiment of the present disclosure. Specifically, in some examples, one or more operations of flow 1300 may be performed by the PSAP 104, the communication engine 122, and/or the health data authorization request engine 210. At 1302, health data for a user is collected and stored in a secure location. For example, one or more health monitoring devices 108 can collect health data 120 for a user and the health data 120 can be stored in the secure location 302 (e.g., the cloud storage 112, the secured memory 118, or some other secure location). At 1304, the user experiences a medical emergency that is detected by an electronic device associated with the user. For example, a health monitoring device 108 may detect if the user has been knocked unconscious, is suffering from dangerously low blood sugar, is having a heart attack, or is otherwise incapacitated or potentially suffering a life-threatening medical emergency. In some examples, the health monitoring device 108 that detected the medical emergency can communicate the detection of the health emergency to the electronic device 102. At 1306, the electronic device associated with the user sends a communication to a PSAP along with authorization to access the health data sorted in the secure location. For example, the health monitoring device 108 or the electronic device 102 can sent a communication to the PSAP 104 regarding the medical emergency along with the authorization (e.g., health data authorization 308) to access the health data 120 stored in the secure location 302. At 1308, the PSAP communicates the authorization to one or more first responders responding to the communication from the electronic device to enable the one or more first responders to access the health data and any updated health data. For example, the PSAP 104 can communication the authorization to access the health data 120 stored in the secure location 302 to the first responder device 106 and the first responder device 106 can use the authorization to access the health data 120 and any updated health data 120 stored in the secure location 302.

Figure 14:
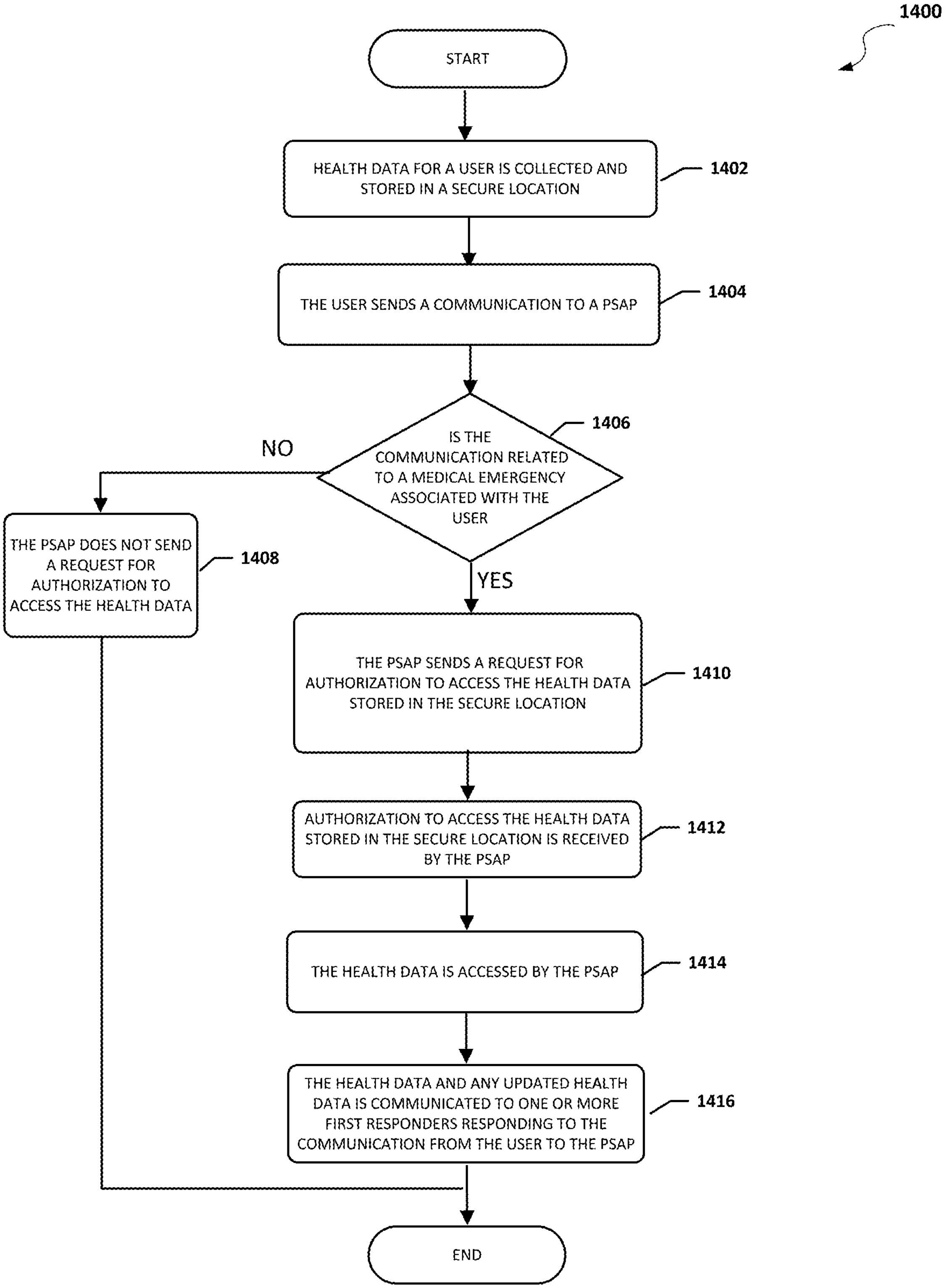
FIG. 14 is a simplified flowchart illustrating potential operations to help enable near real time health data communication to a PSAP and/or one or more first responders, in accordance with an embodiment of the present disclosure.

Turning to FIG. 14, FIG. 14 is example flowchart illustrating possible operations of a flow 1400 that may be associated with potential operations to help enable near real time communication of health data to a PSAP and/or one or more first responders, in accordance with an embodiment of the present disclosure. Specifically, in some examples, one or more operations of flow 1400 may be performed by the PSAP 104, the communication engine 122, and/or the health data authorization request engine 210. At 1402, health data for a user is collected and stored in a secure location. For example, one or more health monitoring devices 108 can collect health data 120 for a user and the health data 120 can be stored in the secure location 302 (e.g., the cloud storage 112, the secured memory 118, or some other secure location). At 1404, the user sends a communication to a PSAP. For example, the communication may be a voice call, text (e.g. SMS message), video call, or some other communication from the electronic device 102 to the PSAP 104. At 1406, it is determined whether or not the communication is related to a medical emergency associated with the user. For example, the PSAP operator may determine if the communication is related to a medical emergency, the communication engine 122 may determine if the communication is related to a medical emergency, the health data authorization request engine 210 may determine if the communication is related to a medical emergency, or some other means may be used to determine if the communication is related to a medical emergency (e.g., an interactive voice response (IVR) system, chatbot, artificial intelligence (AI), etc.). If the communication is not related to a medical emergency associated with the user, the PSAP does not send a request for authorization to access the health data, as in 1408. For example, if the communication is about a crime, vehicle accident that does not involve the user, or some other communication that does not involve a medical emergency associated with the user, the PSAP and/or first responders do not need the health data 120 of the user and to respect the privacy of the user, access to the health data 120 is not requested.

If the communication is related to a medical emergency associated with the user, the PSAP sends a request for authorization to access the health data stored in the secure location, as in 1410. For example, if the communication is related to a medical emergency associated with the user and the PSAP operator dispatches first responders to the user to help the user with the medical emergency, the PSAP 104 can communicate a request for the authorization to access the health data 120 stored in the secure location 302. At 1412, authorization to access the health data stored in the secure location is received by the PSAP. For example, the PSAP 104 can receive a key, certificate, password, token, or some other type of authorization (e.g., health data authorization 308) that will allow the PSAP 104 to access the health data 120 in the secure location 302. At 1414, the health data is access by the PSAP. For example, the PSAP 104 can use the authorization to access the health data 120 in the secure location 302. In some examples, the PSAP does not access the health data 120 and instead communicates the authorization to the first responder device 106 to allow the first responder device 106 to access the health data 120. At 1416, the health data and any updated health data is communication to one or more first responders responding to the communication from the user to the PSAP. For example, the PSAP 104 can communicate the health data 120 and any updated health data 120 to the first responder device 106.

Figure 15:
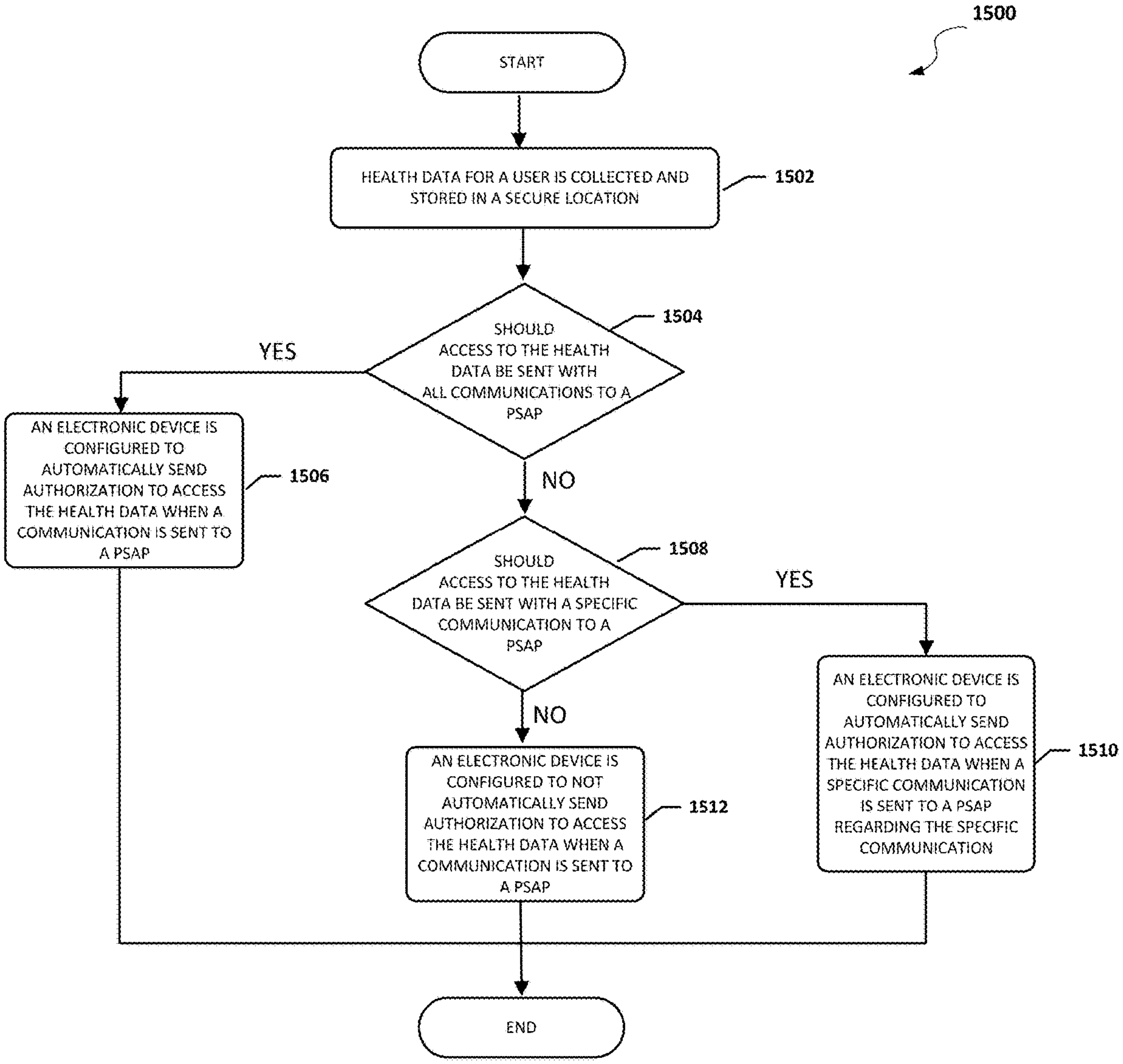
FIG. 15 is a simplified flowchart illustrating potential operations to help enable near real time health data communication to a PSAP and/or one or more first responders, in accordance with an embodiment of the present disclosure.

Turning to FIG. 15, FIG. 15 is example flowchart illustrating possible operations of a flow 1500 that may be associated with potential operations to help enable near real time communication of health data to a PSAP and/or one or more first responders, in accordance with an embodiment of the present disclosure. Specifically, in some examples, one or more operations of flow 1500 may be performed by the PSAP 104, the communication engine 122, and/or the health data authorization request engine 210. At 1502, health data for a user is collected and stored in a secure location. For example, one or more health monitoring devices 108 can collect health data 120 for a user and the health data 120 can be stored in the secure location 302 (e.g., the cloud storage 112, the secured memory 118, or some other secure location). At 1504, the system determines if access to the health data should be sent with all communications to a PSAP. For example, through a user interface on the electronic device 102, the user of the electronic device 102 can choose whether or not access to the health data 120 should be sent with any communication to the PSAP 104. If access to the health data should be sent with all communications to a PSAP, the electronic device is configured to automatically send authorization to access the health data when a communication is sent to a PSAP, as in 1506. For example, when the electronic device 102 sends a communication to the PSAP, even a communication that is not related to a medical emergency associated with the user (e.g., a car crash that does not involve the user), the authorization to access the health data 120 is automatically sent along with the communication.

If the system determines access to the health data should not be sent with all communications to a PSAP, the system determines if access to the health data should be sent with a specific communication to a PSAP, as in 1508. For example, through a user interface on the electronic device 102, the user of the electronic device 102 can choose whether or not access to the health data 120 should be sent with a specific communication, for example, a medical emergency associated with the user, to the PSAP 104. If the system determines access to the health data should be sent with a specific communication to a PSAP, an electronic device is configured to automatically send authorization to access the health data when a specific communication is sent to a PSAP regarding the specific communication, as in 1510. For example, when the electronic device 102 sends a communication regarding a medical emergency related to or associated with the user to the PSAP 104, the authorization to access the health data 120 is automatically sent along with the communication regarding the medical emergency related associated with the user. If the system determines access to the health data should not be sent with a specific communication to a PSAP, an electronic device is configured to not automatically send authorization to access the health data when a communication is sent to a PSAP, as in 1512. By allowing the user to pre-program or pre-provision when the authorization to access the health data is automatically sent to a PSAP, the system can allow the user to determine when their health data is shared.

In the description, various aspects of the illustrative implementations are described using terms commonly employed by those skilled in the art to convey the substance of their work to others skilled in the art. However, it will be apparent to those skilled in the art that the embodiments disclosed herein may be practiced with only some of the described aspects. For purposes of explanation, specific numbers, materials, and configurations are set forth in order to provide a thorough understanding of the illustrative implementations. However, it will be apparent to one skilled in the art that the embodiments disclosed herein may be practiced without the specific details. In other instances, well-known features are omitted or simplified in order not to obscure the illustrative implementations.

In the detailed description, reference is made to the accompanying drawings that form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense. For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C). Reference to "one embodiment" or "an embodiment" in the present disclosure means that a particular feature, structure, or characteristic described in connection with the embodiment is included in at least one embodiment. The appearances of the phrase "in one embodiment" or "in an embodiment" are not necessarily all referring to the same embodiment. Reference to "one example" or "an example" in the present disclosure means that a particular feature, structure, or characteristic described in connection with the embodiment is included in at least one example or embodiment. The appearances of the phrase "in one example" or "in an example" are not necessarily all referring to the same examples or embodiments. The terms "substantially," "close," "approximately," "near," and "about," generally refer to being within +/−20% of a target value based on the context of a particular value as described herein or as known in the art.

As used herein, the term "when" may be used to indicate the temporal nature of an event. For example, the phrase "event 'A' occurs when event 'B' occurs" is to be interpreted to mean that event A may occur before, during, or after the occurrence of event B, but is nonetheless associated with the occurrence of event B. For example, event A occurs when event B occurs if event A occurs in response to the occurrence of event B or in response to a signal indicating that event B has occurred, is occurring, or will occur. Substantial flexibility is provided by the system, apparatus, and method to enable near real time communication of health data to a PSAP and/or one or more first responders in that any suitable arrangements, chronologies, configurations, and timing mechanisms may be provided without departing from the teachings of the present disclosure.

Note that embodiments of the electronic device 102, the PSAP 104, the first responder device 106, the health monitoring device 108, the communication engine 122, and/or the health data authorization request engine 210 may include one or more distinct interfaces, represented by any suitable network interfaces to facilitate communication via the various networks (including both internal and external networks) described herein. Such network interfaces may be inclusive of multiple wired and/or wireless interfaces (e.g., Wi-Fi, WiMax, 3G, 4G, 5G+, white space, 802.11x, satellite, Bluetooth, LTE, GSM/HSPA, CDMA/EVDO, DSRC, CAN, GPS, etc.). Other interfaces, may include physical ports (e.g., Ethernet, USB, HDMI, etc.), interfaces for wired and wireless internal subsystems, and the like. Similarly, each of the electronic device 102, the PSAP 104, the first responder device 106, the health monitoring device 108, the communication engine 122, and/or the health data authorization request engine 210 can also include suitable interfaces for receiving, transmitting, and/or otherwise communicating data or information in a network environment.

The electronic device 102, the PSAP 104, the first responder device 106, the health monitoring device 108, the communication engine 122, and/or the health data authorization request engine 210 and other associated or integrated components can include one or more memory elements for storing information to be used in achieving operations associated with obtaining additional information related to near real time communication of health data to a PSAP and/or one or more first responders, as outlined herein. These devices may further keep information in any suitable memory element (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. The information being tracked, sent, received, or stored in the health data communication system 100 could be provided in any database, register, table, cache, queue, control list, or storage structure, based on particular needs and implementations, all of which could be referenced in any suitable timeframe. Any of the memory or storage options discussed herein should be construed as being encompassed within the broad term 'memory element' as used herein in this Specification.

In example embodiments, the operations for enabling near real time communication of health data to a PSAP and/or one or more first responders, outlined herein, may be implemented by logic encoded in one or more tangible media, which may be inclusive of non-transitory media (e.g., embedded logic provided in an ASIC, digital signal processor (DSP) instructions, software potentially inclusive of object code and source code to be executed by a processor or other similar machine, etc.). In some of these instances, one or more memory elements can store data used for the operations described herein. This includes the memory elements being able to store software, logic, code, or processor instructions that are executed to carry out the near real time communication of health data to a PSAP and/or one or more first responders described in this Specification. Regarding a physical implementation of the electronic device 102, the PSAP 104, the first responder device 106, and the health monitoring device 108, and their associated components such as the communication engine 122, the health data authorization request engine 210, etc., any suitable permutation may be applied based on particular needs and requirements.

Note that with the examples provided herein, interaction may be described in terms of one, two, three, or more elements. However, this has been done for purposes of clarity and example only. In certain cases, it may be easier to describe one or more of the functionalities by only referencing a limited number of elements. It should be appreciated that the system, apparatus, and a method to enable near real time communication of health data to a PSAP and/or one or more first responders and their teachings are readily scalable and can accommodate a large number of components, as well as more complicated/sophisticated arrangements and configurations. Accordingly, the examples provided should not limit the scope or inhibit the broad teachings of the system, apparatus, and method to enable obtaining additional information related to near real time communication of health data to a PSAP and/or one or more first responders and as potentially applied to a myriad of other architectures.

It is also important to note that the operations in the preceding timing diagrams (i.e., FIGS. 3-7) and flow diagrams (i.e., FIGS. 8-21) illustrate only some of the possible correlating scenarios and patterns that may be executed, some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided in that any suitable arrangements, chronologies, configurations, and timing mechanisms may be provided without departing from the teachings of the present disclosure.

Although the present disclosure has been described in detail with reference to particular arrangements and configurations, these example configurations and arrangements may be changed significantly without departing from the scope of the present disclosure. Moreover, certain components may be combined, separated, eliminated, or added based on particular needs and implementations. Additionally, although the system and method have been illustrated with reference to particular elements and operations, these elements and operations may be replaced by any suitable architecture, protocols, and/or processes that achieve the intended functionality of the system and method.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A method, comprising:

receiving, at a public safety answering point (PSAP), from a device, an emergency communication related to a user;

in response to receiving the emergency communication, sending, by the PSAP, a request for authorization to access near real time health data for the user stored in a secure location;

receiving, from the device, the authorization to access the near real time health data for the user, wherein the near real time health data includes at least one biometric reading of at least one health condition of the user, wherein the at least one biometric reading is collected by one or more health monitoring devices associated with the user, and the at least one biometric reading includes at least one of heart rate, temperature, oxygen saturation, blood pressure, blood glucose level, or electrocardiogram (ECG) data;

communicating the authorization to an electronic device that controls access to the secure location to access the near real time health data related to the user; and in response to communicating the authorization to the electronic device that controls access to the secure location, receiving from the secure location, the near real time health data related to the user.

2. The method of claim 1, wherein the near real time health data is a biometric reading of a condition of the user that has been collected within less than five (5) minutes from when the health data is received from the secure location.

3. The method of claim 1, further comprising:

communicating the near real time health data to a first responder responding to the emergency communication.

4. The method of claim 1, further comprising:

communicating the authorization to access the health data related to the user to a first responder to allow the first responder to receive the near real time health data from the secure location.

5. The method of claim 4, wherein the near real time health data of the user that has been collected within less than three (3) minutes from when the health data was received by the first responder.

6. The method of claim 1, wherein the near real time health data related to the user was collected by one or more health monitoring devices associated with the user.

7. The method of claim 1, further comprising:

receiving updated near real time health data related to the user.

8. The method of claim 1, wherein the authorization includes at least one of a key, a certificate, a password, or a token.

9. A system located at a public safety answering point (PSAP), the system comprising:

memory;

at least one processor;

a communication engine located at the PSAP, the communication engine configured to:

receive, from a device, a medical emergency communication related to a user;

determine whether the medical emergency communication is related to a medical emergency associated with the user;

in response to determining the medical emergency communication is related to a medical emergency associated with the user, communicate, from the PSAP, a request for authorization to access near real time health data for the user stored in a secure location, wherein the near real time health data includes at least one biometric reading of at least one health condition of the user, wherein the at least one biometric reading is collected by one or more health monitoring devices associated with the user;

receive, from the device, the authorization to access near real time health data for the user, wherein the authorization includes at least one of a key, a certificate, a password, or a token;

communicate the authorization to an electronic device that controls access to the near real time health data to access the near real time health data related to the user; and receive, the near real time health data related to the user.

10. The system of claim 9, wherein the communication engine is further configured to:

communicate the near real time health data to a first responder responding to the emergency communication.

11. The system of claim 9, wherein the communication engine is further configured to:

communicate the authorization to access the health data related to the user to a first responder to allow the first responder to receive the near real time health data.

12. The system of claim 9, wherein the near real time health data is less than three (3) minutes old.

13. The system of claim 9, wherein the near real time health data is stored in a secure location in cloud storage.

14. The system of claim 9, wherein the near real time health data related to the user was collected by one or more health monitoring devices associated with the user.

15. A method, comprising:

in response to receiving a communication at public safety answering point (PSAP) from a user, in response to determining the communication is related to a medical emergency associated with the user, requesting authorization to access near real time health data for the user from a secure location where the near real time health data is stored, wherein the near real time health data includes at least one biometric reading of at least one health condition of the user, wherein the at least one biometric reading is collected by one or more health monitoring devices associated with the user and includes at least one of heart rate, temperature, oxygen saturation, blood pressure, blood glucose level, or electrocardiogram (ECG) data;

receiving, from a device associated with the user, the authorization to access the near real time health data for the user;

receiving the near real time health data for the user; and communicating the near real time health data for the user to a first responder.

16. The method of claim 15, further comprising:

communicating the authorization to access the near real time health data for the user to the first responder.

17. The method of claim 15, wherein the near real time health data is less than one (1) minute old.

18. The method of claim 15, further comprising:

receiving updated near real time health data related to the user.

19. The method of claim 15, wherein the near real time health data is collected by a health monitoring device associated with the user.

20. The method of claim 15, wherein the authorization to access the near real time health data for the user from the secure location is located on a device that initiated the communication to the PSAP.

* * * * *